US008597654B2

(12) United States Patent
Bryant

(10) Patent No.: US 8,597,654 B2
(45) Date of Patent: *Dec. 3, 2013

(54) ADJUVANT THERAPY WITH AN ANTI-ERBB2 ANTIBODY CONJUGATED TO A MAYTANSINIOD

(75) Inventor: John L. Bryant, Allison Road, PA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,523

(22) Filed: Aug. 8, 2011

(65) Prior Publication Data

US 2012/0003217 A1    Jan. 5, 2012

Related U.S. Application Data

(63) Continuation of application No. 11/400,638, filed on Apr. 6, 2006.

(60) Provisional application No. 60/681,125, filed on May 13, 2005.

(51) Int. Cl.
   *A61K 39/395*   (2006.01)

(52) U.S. Cl.
   USPC .............. 424/181.1; 424/130.1; 424/133.1; 424/141.1; 424/143.1; 424/178.1

(58) Field of Classification Search
   USPC .......... 424/130.1, 133.1, 141.1, 143.1, 178.1, 424/179.1, 181.1
   See application file for complete search history.

(56) References Cited

U.S. PATENT DOCUMENTS

| | | | |
|---|---|---|---|
| 4,935,341 A | 6/1990 | Bargmann |
| 4,968,603 A | 11/1990 | Slamon |
| 5,183,884 A | 2/1993 | Kraus |
| 5,288,477 A | 2/1994 | Bacus |
| 5,401,638 A | 3/1995 | Carney |
| 5,480,968 A | 1/1996 | Kraus |
| 5,514,554 A | 5/1996 | Bacus |
| 5,571,894 A | 11/1996 | Wels |
| 5,587,458 A | 12/1996 | King |
| 5,604,107 A | 2/1997 | Carney |
| 5,641,869 A | 6/1997 | Vandlen |
| 5,648,237 A | 7/1997 | Carter |
| 5,677,171 A | 10/1997 | Hudziak |
| 5,705,157 A | 1/1998 | Greene |
| 5,720,937 A | 2/1998 | Hudziak |
| 5,720,954 A | 2/1998 | Hudziak |
| 5,725,856 A | 3/1998 | Hudziak |
| 5,747,261 A | 5/1998 | King |
| 5,770,195 A | 6/1998 | Hudziak |
| 5,772,997 A | 6/1998 | Hudziak |
| 5,783,186 A | 7/1998 | Arakawa |
| 5,783,404 A | 7/1998 | Koski |
| 5,804,396 A | 9/1998 | Plowman |
| 5,821,337 A | 10/1998 | Carter |
| 5,824,311 A | 10/1998 | Greene |
| 5,837,243 A | 11/1998 | Deo |
| 5,846,749 A | 12/1998 | Slamon |
| 5,856,089 A | 1/1999 | Wang |
| 5,877,305 A | 3/1999 | Huston |
| 5,910,486 A | 6/1999 | Curiel |
| 5,922,845 A | 7/1999 | Deo |
| 5,925,519 A | 7/1999 | Jennsen |
| 5,939,531 A | 8/1999 | Wels |
| 5,977,322 A | 11/1999 | Marks |
| 5,985,553 A | 11/1999 | King |
| 5,994,071 A | 11/1999 | Ross |
| 6,015,567 A | 1/2000 | Hudziak |
| 6,028,059 A | 2/2000 | Curiel |
| 6,054,297 A | 4/2000 | Carter |
| 6,123,939 A | 9/2000 | Shawver |
| 6,127,526 A | 10/2000 | Blank |
| 6,165,464 A | 12/2000 | Hudziak |
| 6,214,388 B1 | 4/2001 | Benz |
| 6,267,958 B1 | 7/2001 | Andya |
| 6,270,765 B1 | 8/2001 | Deo |
| 6,333,169 B1 | 12/2001 | Hudziak |
| 6,333,348 B1 | 12/2001 | Vogel |
| 6,333,398 B1 | 12/2001 | Blank |
| 6,339,142 B1 | 1/2002 | Basey |
| 6,358,682 B1 | 3/2002 | Jaffee |
| 6,387,371 B1 | 5/2002 | Hudziak |
| 6,395,272 B1 | 5/2002 | Deo |
| 6,399,063 B1 | 6/2002 | Hudziak |

(Continued)

FOREIGN PATENT DOCUMENTS

EP    412116    4/1989
EP    494135    9/1989

(Continued)

OTHER PUBLICATIONS

Lu, Y. et al. Journal of the National Cancer Institute, 93 (24): 1852-1857, 2001.*
Aasland et al., *Br. J. Cancer*, 57:358-363 (1988).
Albain et al., *Proceedings of the American Society of Clinical Oncology Thirty-Eighth Annual Meeting*, May 18-21, 2002, Orlando, FL Abstract 143; The ATAC (Arimidex, Tamoxifen Alone or in Combination) Trialists' Group, *Lancet*, 359:2131-39 (2002).
Arteaga et al., *Cancer Res.*, 54:3758-3765 (1994).
Bacus et al., *Cancer Research*, 52:2580-2589 (1992).
Bacus et al., *Molecular Carcinogenesis*, 3:350-362 (1990).
Baselga and Mendelsohn, *Pharmac. Ther.*, 64:127-154 (1994).
Baselga et al., *J. Clin. Oncol.*, 14:737-744 (1996).
Bendell et al., *Cancer*, 97:2972-7 (2003).

(Continued)

*Primary Examiner* — Misook Yu
*Assistant Examiner* — Anne Holleran
(74) *Attorney, Agent, or Firm* — Danielle Pasqualone; Ginger R. Dreger; Arnold & Porter LLP

(57) ABSTRACT

The present application describes adjuvant therapy of non-metastatic breast cancer using an anti-ErbB2 antibody conjugated to a maytansinoid.

15 Claims, 17 Drawing Sheets

(56) References Cited

U.S. PATENT DOCUMENTS

| | | |
|---|---|---|
| 6,403,630 B1 | 6/2002 | Danenberg |
| 6,407,213 B1 | 6/2002 | Carter |
| 6,417,335 B1 | 7/2002 | Basey |
| 6,458,356 B1 | 10/2002 | Arakawa |
| 6,489,447 B1 | 12/2002 | Basey |
| 6,512,097 B1 | 1/2003 | Marks |
| 6,573,043 B1 | 6/2003 | Cohen |
| 6,582,919 B2 | 6/2003 | Danenberg |
| 6,602,670 B2 | 8/2003 | Danenberg |
| 6,627,196 B1 | 9/2003 | Baughman |
| 6,632,979 B2 | 10/2003 | Erickson |
| 6,685,940 B2 | 2/2004 | Andya |
| 6,719,971 B1 | 4/2004 | Carter |
| 6,733,752 B1 | 5/2004 | Greene et al. |
| 6,767,541 B2 | 7/2004 | Slamon |
| 6,797,814 B2 | 9/2004 | Blank |
| 6,800,738 B1 | 10/2004 | Carter et al. |
| 6,821,515 B1 | 11/2004 | Cleland |
| 6,884,418 B1 | 4/2005 | Shawver et al. |
| 7,097,840 B2 * | 8/2006 | Erickson et al. ............ 424/178.1 |
| 7,303,749 B1 | 12/2007 | Chari |
| 7,501,122 B2 | 3/2009 | Adams et al. ............... 424/143.1 |
| 7,575,748 B1 | 8/2009 | Erickson et al. |
| 7,601,354 B2 | 10/2009 | Chari |
| 7,989,598 B2 | 8/2011 | Steeves et al. |
| 8,088,387 B2 | 1/2012 | Steeves et al. |
| 8,142,784 B2 | 3/2012 | Ebens, Jr. et al. |
| 8,163,888 B2 | 4/2012 | Steeves et al. |
| 8,198,417 B2 | 6/2012 | Steeves et al. |
| 8,337,856 B2 | 12/2012 | Blattler et al. |
| RE43,899 E | 1/2013 | Blattler et al. |
| 2002/0031515 A1 | 3/2002 | Caligiuri |
| 2002/0051785 A1 | 5/2002 | Salmon |
| 2002/0064785 A1 | 5/2002 | Mass |
| 2002/0076408 A1 | 6/2002 | Buchsbaum |
| 2002/0076695 A1 | 6/2002 | Ross |
| 2002/0090662 A1 | 7/2002 | Ralph |
| 2002/0141993 A1 | 10/2002 | Ashkenazi |
| 2002/0142328 A1 | 10/2002 | Danenberg |
| 2002/0155527 A1 | 10/2002 | Stuart |
| 2002/0192211 A1 | 12/2002 | Hudziak |
| 2002/0192652 A1 | 12/2002 | Danenberg |
| 2003/0022918 A1 | 1/2003 | Horak |
| 2003/0059790 A1 | 3/2003 | Jaffee |
| 2003/0068318 A1 | 4/2003 | O'Brien |
| 2003/0086924 A1 | 5/2003 | Sliwkowski |
| 2003/0103973 A1 | 6/2003 | Rockwell |
| 2003/0108545 A1 | 6/2003 | Rockwell |
| 2003/0134344 A1 | 7/2003 | Mass |
| 2003/0144252 A1 | 7/2003 | Furr |
| 2003/0147884 A1 | 8/2003 | Paton |
| 2003/0152572 A1 | 8/2003 | Homma |
| 2003/0152987 A1 | 8/2003 | Cohen |
| 2003/0157097 A1 | 8/2003 | Noguchi |
| 2003/0165840 A1 | 9/2003 | Danenberg |
| 2003/0170234 A1 | 9/2003 | Hellmann |
| 2003/0170235 A1 | 9/2003 | Cohen ........................ 424/143.1 |
| 2003/0175845 A1 | 9/2003 | Kalbag |
| 2003/0190689 A1 | 10/2003 | Crosby |
| 2003/0202973 A1 | 10/2003 | Pieczenik |
| 2003/0211530 A1 | 11/2003 | Danenberg |
| 2003/0228663 A1 | 12/2003 | Lowman |
| 2004/0013297 A1 | 1/2004 | Lo |
| 2004/0013667 A1 | 1/2004 | Kelsey |
| 2004/0014694 A1 | 1/2004 | Chakroun |
| 2004/0024815 A1 | 2/2004 | Kawase |
| 2004/0082047 A1 | 4/2004 | Emery |
| 2004/0106161 A1 | 6/2004 | Bossenmaier |
| 2004/0138160 A1 | 7/2004 | Naito |
| 2004/0209290 A1 | 10/2004 | Cobleigh |
| 2004/0236078 A1 | 11/2004 | Carter |
| 2004/0258685 A1 | 12/2004 | Brunetta |
| 2005/0002928 A1 | 1/2005 | Hellmann |
| 2005/0276812 A1 | 12/2005 | Ebens, Jr. et al. |
| 2008/0171040 A1 | 7/2008 | Ebens, Jr. et al. |
| 2008/0171865 A1 | 7/2008 | Steeves et al. |
| 2011/0281856 A1 | 11/2011 | Chari et al. |

FOREIGN PATENT DOCUMENTS

| | | |
|---|---|---|
| EP | 444181 | 8/1990 |
| EP | 1006194 | 8/1990 |
| EP | 502812 | 1/1992 |
| EP | 554441 | 8/1992 |
| EP | 656367 | 8/1992 |
| EP | 616812 | 3/1993 |
| EP | 599274 | 11/1993 |
| EP | 711565 | 11/1995 |
| EP | 1357132 | 4/2003 |
| WO | WO 89/10412 | 11/1989 |
| WO | WO 91/02062 | 2/1991 |
| WO | WO 91/05264 | 4/1991 |
| WO | WO 93/03741 | 3/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 94/00136 | 1/1994 |
| WO | WO 94/22478 | 10/1994 |
| WO | WO 96/07321 | 3/1996 |
| WO | WO 96/16673 | 6/1996 |
| WO | WO 96/40789 | 12/1996 |
| WO | WO 97/00271 | 1/1997 |
| WO | WO 97/20858 | 6/1997 |
| WO | WO 97/38731 | 10/1997 |
| WO | WO 98/02463 | 1/1998 |
| WO | WO 98/17797 | 4/1998 |
| WO | WO 98/18489 | 5/1998 |
| WO | WO 98/33914 | 8/1998 |
| WO | WO 98/45479 | 10/1998 |
| WO | WO 99/31140 | 6/1999 |
| WO | WO 99/48527 | 9/1999 |
| WO | WO 99/55367 | 11/1999 |
| WO | WO 00/61145 | 10/2000 |
| WO | WO 00/61185 | 10/2000 |
| WO | WO 00/69460 | 11/2000 |
| WO | WO 00/78347 | 12/2000 |
| WO | WO 01/00238 | 1/2001 |
| WO | WO 01/00244 | 1/2001 |
| WO | WO 01/00245 | 1/2001 |
| WO | WO 01/05425 | 1/2001 |
| WO | WO 01/09187 | 2/2001 |
| WO | WO 01/15730 | 3/2001 |
| WO | WO 01/20033 | 3/2001 |
| WO | WO 01/21192 | 3/2001 |
| WO | WO 01/32155 | 5/2001 |
| WO | WO 01/53354 | 7/2001 |
| WO | WO 01/56604 | 8/2001 |
| WO | WO 01/64246 | 9/2001 |
| WO | WO 01/76586 | 10/2001 |
| WO | WO 01/76630 | 10/2001 |
| WO | WO 01/87334 | 11/2001 |
| WO | WO 01/87336 | 11/2001 |
| WO | WO 01/89566 | 11/2001 |
| WO | WO 02/05791 | 1/2002 |
| WO | WO 02/09754 | 2/2002 |
| WO | WO 02/11677 | 2/2002 |
| WO | WO 02/44413 | 6/2002 |
| WO | WO 02/45653 | 6/2002 |
| WO | WO 02/055106 | 7/2002 |
| WO | WO 02/070008 | 9/2002 |
| WO | WO 02/087619 | 11/2002 |
| WO | WO 02/089842 | 11/2002 |
| WO | WO 03/006509 | 1/2003 |
| WO | WO 03/012072 | 2/2003 |
| WO | WO 03/028638 | 4/2003 |
| WO | WO 03/041736 | 5/2003 |
| WO | WO 03/086467 | 10/2003 |
| WO | WO 03/087131 | 10/2003 |
| WO | WO 2004/000094 | 12/2003 |
| WO | WO 2004/008099 | 1/2004 |
| WO | WO 2004/024866 | 3/2004 |

(56) References Cited

FOREIGN PATENT DOCUMENTS

| WO | WO 2004/048525 | 6/2004 |
| WO | WO 2004/053497 | 6/2004 |
| WO | WO 2004/063709 | 7/2004 |

OTHER PUBLICATIONS

Borst et al., *Gynecol. Oncol.*, 38:364 (1990).
Burstein et al., *J. Clin. Oncol.*, 19(10); 2722-2730 (2001).
Carraway and Cantley, *Cell*, 78:5-8 (1994).
Carraway et al., *Nature*, 387: 512-516 (1997).
Chang et al., *Nature*, 387 509-512 (1997).
Clayton et al., *Brit. J. Cancer*, 91:639-43 (2004).
Cohen et al., *Oncogene*, 4:81-88 (1989).
Cronin et al., *Am. J. Path.*, 164(1):35-42 (2004).
Drebin et al., *Cell*, 41:695-706 (1985).
Drebin et al., *Oncogene*, 2:273-277 (1988).
D'souza et al., *Proc. Natl. Acad. Sci.*, 91:7202-7206 (1994).
Earp et al., *Breast Cancer Research and Treatment*, 35:115-132 (1995).
Esteva et al., *J. Clin. Oncol.*, 20(7):1800-1808 (2002).
Ewer et al., *Proc. Am. Soc. Clin. Oncol.*, (abstr. 489) (2002).
Extra, JM, *Breast Cancer Res Treat*, 82 (Suppl 1):217 (2003).
Fendly et al., *Cancer Research*, 50:1550-1558 (1990).
Fukushige et al., *Mol Cell Biol.*, 6:955-958 (1986).
Geyer et al., *26th Annual San Antonio Breast Cancer Symposium (SABCS)*, Dec. 2003, Abstract 12; Perez et al., *Proc. ASCO*, 2005, Abstract 556.
Groenen et al., *Growth Factors*, 11:235-257 (1994).
Gu et al., *Cancer Lett.*, 99:185-9 (1996).
Guerin et al., *Oncogene Res.*, 3:21-31 (1988).
Hancock et al., *Cancer Res.*, 51:4575-4580 (1991).
Harari et al., *Oncogene*, 18:2681-89 (1999).
Harwerth et al., *J. Biol. Chem.*, 267:15160-15167 (1992).
Holmes et al., *Science*, 256:1205-1210 (1992).
Hudziak et al., *Mol. Cell. Biol.*, 9(3):1165-1172 (1989).
Jones, A., *Annals of Oncology*, 14:1697-1794 (2003).
Kasprzyk et al., *Cancer Research*, 52:2771-2776 (1992).
Kern et al., *Cancer Res.*, 50:5184 (1990).
King et al., *Science*, 229:974 (1985).
Klapper et al., *Oncogene*, 14:2099-2109 (1997).
Kotts et al., *In Vitro*, 26(3):59A (1990).
Kraus et al., *PNAS (USA)*, 86:9193-9197 (1989).
Kumar et al., *Mol. Cell. Biol.*, 11(2):979-986 (1991).
Lee et al., *Pharm. Rev.*, 47: 51-85 (1995).
Lemke, G., *Molec. & Cell. Neurosci.*, 7:247-262 (1996).
Levi et al., *Journal of Neuroscience*, 15: 1329-1340 (1995).
Lewis et al., *Cancer Immunol. Immunother.* 37:255-263 (1993).
Lewis et al., *Cancer Research*, 56:1457-1465 (1996).
Leyland-Jones et al., *J. Clin. Oncol.*, 21(21):3965-3971 (2003).
Limentani et al., *Breast Cancer Res Treat*, 76:abstract 162 (2002).
Ma et al., *Cancer Cell*, 5:607-616 (2004).
Maier et al., *Cancer Res.*, 51:5361-5369 (1991).
Masui et al., *Cancer Research*, 44:1002-1007 (1984).
McCann et al., *Cancer*, 65:88-92 (1990).
McKenzie et al., *Oncogene*, 4:543-548 (1989).
Miller et al., *Oncology*, 15(2):38-40 (2001).
Morrissey et al., *Proc. Natl. Acad. Sci. USA*, 92:1431-1435 (1995).
Myers et al., *Meth. Enzym.*, 198:277-290 (1991).
NSABP Trial for Herceptin. *San Antonio Breast Cancer Symposium*, 2002; Roche PC et al., *J. Natl. Cancer Inst.*, 94(11):855-7 (2002).
O'Shaughnessy et al., *Breast Cancer Res Treat*, 69:302 abstract 523 (2001).
Owens et al., *Breast Cancer Res Treat*, 76:S68 abstract 236 (2002).
Paik et al., *J. Natl. Cancer Inst.*, 914:852-854 (2002).
Paik et al., *J. Natl. Cancer Inst.*, 92(24):1991-1998 (2000).
Park et al., *Cancer Res.*, 49:6605 (1989).
Pauletti et al., *J Clin Oncol*, 18:3651-64 (2000).
Pegram et al., *J Clin Oncol*, 16:209-71 (1998).
Pegram et al., *J. Natl. Cancer Inst.*, 96(10):759-69 (2004).
Pietras et al., *Oncogene*, 9:1829-1838 (1994).
Plowman et al., *Nature*, 366:473-475 (1993).
Plowman et al., *Proc. Natl. Acad. Sci. USA*, 90:1746-1750 (1993).
Press et al., *J Clin Oncol*, 1997;15:2894-904 (1997).
Robert et al., *Ann. Oncol.*, 15(suppl 3):39 (abstract 144P); (2004).
Ross et al., *Cancer*, 79:2162-70 (1997).
Ross el al., *Hum. Pathol.*, 28:827-33 (1997).
Sadasivan et al., *J. Urol.*, 150:126-31 (1993).
Sarup et al., *Growth Regulation*, 1:72-82, (1991).
Schaefer et al., *Oncogene*, 15:1385-1394, (1997).
Scott et al., *J. Biol. Chem.*, 266:14300-5 (1991).
Seidman et al., *J. Clin. Oncol.*, 20:1215-21 (2002).
Shawver et al., *Cancer Res.*, 54:1367-1373 (1994).
Shepard et al., *J. Clin. Immunol.*, 11(3):117-127 (1991).
Slamon et al. pp. 177-182, (1987).
Slamon et al., *N. Engl. J. of Med*, 344:783-791, (2001).
Slamon et al., *Science*, 244:707-712, (1989).
Sliwkowski et al., *J. Biol. Chem.*, 269(20):14661-14665, (1994).
Stancovski et al., *PNAS (USA)*, 88:8691-8695, (1991).
Tagliabue et al., *Int. J. Cancer*, 47:933-937, (1991).
Theodoulou et al., *Proc Am Soc Clin Oncol*, 21:216 abstract 216 (2002).
Untch et al,. *Eur. J. Cancer*, 40: 988-97 (2004b).
Vitetta et al., *Cancer Research*, 54:5301-5309, (1994).
Weiner et al., *Cancer Res.*, 50:421-425, (1990).
Williams et al., *Pathobiology*, 5:46-52, (1991).
Wong et al., *Breast Cancer Res Treat*, 82(Suppl 1):444 (2003).
Wu et al., *J. Clin. Invest.*, 95:1897-1905 (1995).
Xu et al., *Int. J. Cancer*, 53:401-408 (1993).
Yardley et al., *Breast Cancer Res Treat*, 76:S113 abstract 439 (2002).
Yokota et al., *Lancet*, 1:765-767 (1986).
Yonemura et al., *Cancer Res.*, 51:034-1038, (1991).
Zhang et al., *PNAS (USA)*, 94(18):9562-7 (1997).
Zhau et al., *Mol. Carcinog.*, 3:254-257 (1990).
Sledge, G.W., et al. Breast Cancer Res. Treat., 69: 209, 2001; abstract #4.
Gradishar, W.J. et al., Int. J. Clin. Oncol. 8; 230-247, 2003.
Mohsin, S.K. et al. Journal of Clinical Oncology, 23(11):2460-2468, Apr. 10, 2005.
Guarneri, V. et al., European Journal of Nuclear Medicine and Molecular Imaging, 31: 5149-5161, 2004.
Van Pelt, A.E., et al, Clinical Breast Cancer, 4(5): 348-353, 2003.
Bozionellou et al., "Trastuzumab Administration Can Effectively Target Chemotherapy-Resistant Cytokeratin-19 Messenger RNA—Positive Tumor Cells in the Peripheral Blood and Bone Marrow of Patients with Breast Cancer"; *Clin Cancer Res 2004*; 10:8185-8194.
Braun et al., "erbB2 Overexpression on Occult Metastatic Cells in Bone Marrow Predicts Poor Clinical Outcome of Stage I-III Breast Cancer Patients"; *Cancer Res 2001*; 61:1890-1895.
Katsumata et al., "Prevention of breast tumour development in vivo by downregulation of the p185[neu] receptor"; *Nature Medicine*, vol. 1, No. 7, Jul. 7, 1995, pp. 644-648.
Meng et al., "HER-2 gene amplification can be acquired as breast cancer progresses", *PNAS.org*, vol. 101, No. 25, Jun. 22, 2004, 9393-9398.
Osband et al., "Problems in the investigational study and clinical use of cancer immunotherapy", *Immunology Today*, vol. 1, No. 6, 1990, 193-195.
Pantel et al., "Differential Expression of Proliferation-Associated Molecules in Individual Micrometastatic Carcinoma Cells", *Journal of the National Cancer Institute*, vol. 85, No. 17, Sep. 1, 1993, 1419-1424.
Pantel et al., "Meeting Report: Conference on Cancer Micrometastasis: Biology, Methodology and Clinical Significance", *International Journal of Oncology 3*; 1993, 1019-1022.
Pantel et al., "Overexpression of the erbB2 oncogene product in bone marrow micrometastases from human adenocarcinomas—correlation to tumor progression", *International Symposium Clinical and Scientific Aspects of HER-2 / Neu / ERB-B2*; Jan. 12, 1991, 11 pgs.
Slides from Pantel et al., "Overexpression of the erbB2 oncogene product in bone marrow micrometastases from human adenocarcinomas—correlation to tumor progression", *International Symposium Clinical and Scientific Aspects of HER-2 / NEU / ERB-B2*; Jan. 12, 1991, 9 pgs.

(56) References Cited

OTHER PUBLICATIONS

Riethmuller et al., "Monoclonal antibodies in the detection and therapy of micrometastatic epithelial cancers", *Current Opinion in Immunology*, 1992, 4:647-655.

Riethmuller et al., "Randomized trial of monoclonal antibody for adjuvant therapy of resected Dukes' C colorectal carcinoma", *Lancet*, vol. 343, May 14, 1994, 1177-1183.

Schlimok et al, "Micrometastatic cancer cells in bone marrow: In vitro detection with anti-cytokeratin and in vivo labeling with anti-17-1A monoclonal antibodies", *Proc. Nat'. Acad. Sci. USA* vol. 84, Dec. 1987 Medical Sciences, 8672-8676.

U.S. Appl. No. 13/305,042, filed Nov. 28, 2011, Blattler et al.

Junttila, T.J., et al., "Trastuzumab-DM1 (T-DM1) retains all the mechanisms of action of trastuzumab and efficiently inhibits growth of lapatinib insensitive breast cancer", *Breast Cancer Res. Treat* (2011) 128:347-356.

Lewis Phillips, Gail D., et al., "Targeting HER2-Positive Breast Cancer with Trastuzumab-DM1, an Antibody-Cytotoxic Drug Conjugate", *Cancer Res* 2008; 68:9280-9290.

J. Jasinska et al., "Inhibition of Tumor Cell Growth by Antibodied Induced After Vaccination with Peptides Derived from the Extracellular Domain of Her-2/NEU", *Int. J. Cancer*: 107, 976-983 (2003).

Y. Yip et al., "Identification of Epitope Regions Recognized by Tumor Inhibitory and Stimulatory Anti-ErbB-2 Monoclonal Antibodies: Implications for Vaccine Designs[1]", *The Journal of Immunology*, 166: 5271-5278 (2001).

KADCYLA Prescribing Information, Feb. 2013, pp. 1-22.

\* cited by examiner

LIGHT CHAIN

HEAVY CHAIN

```
1                           15                          30                          45
EVQLVESGGGLVQPGGSLRLSCAASGFNIKDTYIHWVRQAPGKGL
46                          60                          75                          90
EWVARIYPTNGYTRYADSVKGRFTISADTSKNTAYLQMNSLRAED
91                          105                         120                         135
TAVYYCSRWGGDGFYAMDYWGQGTLVTVSSASTKGPSVFPLAPSS
136                         150                         165                         180
KSTSGGTAALGCLVKDYFPEPVTVSWNSGALTSGVHTFPAVLQSS
181                         195                         210                         225
GLYSLSSVVTVPSSSLGTQTYICNVNHKPSNTKVDKKVEPKSCDK
226                         240                         255                         270
THTCPPCPAPELLGGPSVFLFPPKPKDTLMISRTPEVTCVVVDVS
271                         285                         300                         315
HEDPEVKFNWYVDGVEVHNAKTKPREEQYNSTYRVVSVLTVLHQD
316                         330                         345                         360
WLNGKEYKCKVSNKALPAPIEKTISKAKGQPREPQVYTLPPSREE
361                         375                         390                         405
MTKNQVSLTCLVKGFYPSDIAVEWESNGQPENNYKTTPPVLDSDG
406                         420                         435                         449
SFFLYSKLTVDKSRWQQGNVFSCSVMHEALHNHYTQKSLSLSPG
```

FIG. 2B

NSABP B-31

Control: AC →T

Arm 1 ■■■■ ● ● ● ●

Arm 2 ■■■■ ● ● ● ● ○○○○○○○○○○○○○○○○○○○○○○○○○○○○○○○○○○○○○○○○○○○○○○○○○○○

NCCTG N9831

Investigational: AC →T+H

Arm A ■■■■ ●●●●●●●●●●●●

Arm B ■■■■ ●●●●●●●●●●●● ○○○○○○○○○○○○○○○○○○○○○○○○○○○○○○○○○○○○○○○○○○○○○○○○○○

Arm C ■■■■ ●●●●●●●●●●●● ○○○○○○○○○○○○○○○○○○○○○○○○○○○○○○○○○○○○○○○○○○○○○○○○○○

■ = doxorubicin/cyclophosphamide (AC) 60/600 mg/m² q 3 wk x 4

● = paclitaxel (T) 175 mg/m² q 3 wk x 4

●(small) = paclitaxel (T) 80 mg/m²/wk x 12

○ = trastuzumab (H) 4 mg/kg LD + 2 mg/kg/wk x 51

FIG. 4A

PATIENT AND TUMOR CHARACTERISTICS (%)

| | AC→PACLITAXEL | | AC→PACLITAXEL + TRASTUZUMAB | |
|---|---|---|---|---|
| | 872 B-31 | 807 N9831 | 864 B-31 | 808 N9831 |
| AGE | | | | |
| <50 | 52 | 51 | 51 | 50 |
| 50-59 | 34 | 34 | 32 | 32 |
| ≥60 | 15 | 15 | 16 | 18 |
| NO. POS NODES | | | | |
| 0 | 0 | 13 | 0 | 11 |
| 1-3 | 57 | 48 | 57 | 50 |
| 4-9 | 29 | 25 | 29 | 25 |
| 10+ | 14 | 15 | 14 | 14 |
| HORMONE RECEPTORS | | | | |
| ER+ | 53 | 52 | 51 | 51 |
| ER- | 47 | 46 | 48 | 48 |
| PR+ | 41 | 41 | 39 | 39 |
| PR- | 58 | 57 | 60 | 60 |
| TUMOR SIZE | | | | |
| ≤2.0 cm. | 41 | 40 | 37 | 38 |
| 2.1-4.0 cm. | 43 | 46 | 44 | 47 |
| >4.0 cm. | 14 | 13 | 17 | 14 |

FIG. 5

SUMMARY OF EFFICACY ENDPOINT ANALYSES

| Endpoint | HR | 95% CI | 2P | $N_1$ | $N_2$ | Total |
|---|---|---|---|---|---|---|
| DFS (primary) | 0.48 | 0.39 to 0.595 | $3\times10^{-12}$ | 261 | 134 | 395 |
| Time to Recurrence | 0.47 | 0.38 to 0.59 | $9\times10^{-12}$ | 235 | 117 | 352 |
| Time to Distant Recurrence | 0.47 | 0.37 to 0.60 | $8\times10^{-10}$ | 194 | 96 | 290 |
| Survival | 0.67 | 0.48 to 0.93 | 0.015 | 92 | 62 | 154 |
| Breast Cancer Specific Surv | 0.66 | 0.47 to 0.94 | 0.021 | 79 | 53 | 132 |
| Contralateral BC | 0.64 | 0.18 to 2.27 | 0.49 | 6 | 4 | 10 |
| Other 2nd Primary Cancer | 0.29 | 0.12 to 0.72 | 0.0046 | 20 | 6 | 26 |

FIG. 12

AMINO ACID SEQUENCE FOR PERTUZUMAB LIGHT CHAIN

AMINO ACID SEQUENCE FOR PERTUZUMAB HEAVY CHAIN

```
          10         20         30         40         50         60
          |          |          |          |          |          |
  1 — EVQLVESGGGLVQPGGSLRLSCAASGFTFTDYTMDWVRQAPGKGLEWVADVNPNSGGSIY
          70         80         90        100        110        120
          |          |          |          |          |          |
     NQRFKGRFTLSVDRSKNTLYLQMNSLRAEDTAVYYCARNLGPSFYFDYWGQGTLVTVSSA
         130        140        150        160        170        180
          |          |          |          |          |          |
     STKGPSVFPLAPSSKSTSGGTAALGCLVKDYFPEPVTVSWNSGALTSGVHTFPAVLQSSG
         190        200        210        220        230        240
          |          |          |          |          |          |
     LYSLSSVVTVPSSSLGTQTYICNVNHKPSNTKVDKKVEPKSCDKTHTCPPCPAPELLGGP
         250        260        270        280        290        300
          |          |          |          |          |          *
     SVFLFPPKPKDTLMISRTPEVTCVVVDVSHEDPEVKFNWYVDGVEVHNAKTKPREEQYNS
         310        320        330        340        350        360
          |          |          |          |          |          |
     TYRVVSVLTVLHQDWLNGKEYKCKVSNKALPAPIEKTISKAKGQPREPQVYTLPPSREEM
         370        380        390        400        410        420
          |          |          |          |          |          |
     TKNQVSLTCLVKGFYPSDIAVEWESNGQPENNYKTTPPVLDSDGSFFLYSKLTVDKSRWQ
         430        440        448
          |          |          |
     QGNVFSCSVMHEALHNHYTQKSLSLSPG
```

FIG. 14B

ADJUVANT THERAPY WITH AN ANTI-ERBB2 ANTIBODY CONJUGATED TO A MAYTANSINIOD

CROSS-REFERENCE TO RELATED APPLICATIONS

This application is a continuation of U.S. application Ser. No. 11/400,638, filed Apr. 6, 2006, which is a non-provisional application filed under 37 CFR 1.53(b)(1), claiming priority under 35 USC §119(e) and the benefit of U.S. Provisional Patent Application Ser. No. 60/681,125 filed on May 13, 2005, the entire disclosures of which are hereby expressly incorporated by reference.

FIELD OF THE INVENTION

The present invention concerns adjuvant therapy of non-metastatic breast cancer using HERCEPTIN®.

BACKGROUND OF THE INVENTION

HER Receptors and Antibodies Thereagainst

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn, *Pharmac. Ther.*, 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al., *Cancer Research*, 44:1002-1007 (1984); and Wu et al., *J. Clin. Invest.*, 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet*, 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al., *Br. J. Cancer*, 57:358-363 (1988); Williams et al., *Pathobiology*, 59:46-52 (1991); and McCann et al., *Cancer*, 65:88-92 (1990). HER2 may be overexpressed in prostate cancer (Gu et al., *Cancer Lett.*, 99:185-9 (1996); Ross et al., *Hum. Pathol.*, 28:827-33 (1997); Ross et al., *Cancer*, 79:2162-70 (1997); and Sadasivan et al., *J. Urol.*, 150:126-31 (1993)).

HER2 amplification/overexpression is an early event in breast cancer that is associated with aggressive disease and poor prognosis. HER2 gene amplification is found in 20-25% of primary breast tumors (Slamon et al., *Science*, 244:707-12 (1989); Owens et al., *Breast Cancer Res Treat*, 76:S68 abstract 236 (2002)). HER2 positive disease correlates with decreased relapse-free and overall survival (Slamon et al., *Science*, 235:177-82 (1987); Pauletti et al., *J Clin Oncol*, 18:3651-64 (2000)). Amplification of the HER2 gene is associated with significantly reduced time to relapse and poor survival in node-positive disease (Slamon et al. (1987); Pauletti et al. (2000)) and poor outcome in node-negative disease (Press et al., *J Clin Oncol*, 1997; 15:2894-904 (1997); Pauletti et al. (2000)).

Antibodies directed against the rat p185$^{neu}$ and human HER2 protein products have been described.

Drebin and colleagues have raised antibodies against the rat neu gene product, p185$^{neu}$. See, for example, Drebin et al., *Cell*, 41:695-706 (1985); Myers et al., *Meth. Enzym.*, 198: 277-290 (1991); and WO94/22478. Drebin et al., *Oncogene*, 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.*, 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al., Cancer Research, 50:1550-1558 (1990); Kotts et al., In Vitro, 26(3):59A (1990); Sarup et al., *Growth Regulation*, 1:72-82 (1991); Shepard et al., *J. Clin. Immunol.*, 11(3):117-127 (1991); Kumar et al., *Mol. Cell. Biol.*, 11(2):979-986 (1991); Lewis et al., *Cancer Immunol. Immunother.* 37:255-263 (1993); Pietras et al., *Oncogene*, 9:1829-1838 (1994); Vitetta et al., *Cancer Research*, 54:5301-5309 (1994); Sliwkowski et al., *J. Biol. Chem.*, 269(20):14661-14665 (1994); Scott et al., *J. Biol. Chem.*, 266:14300-5 (1991); D'souza et al., *Proc. Natl. Acad. Sci.*, 91:7202-7206 (1994); Lewis et al., *Cancer Research*, 56:1457-1465 (1996); and Schaefer et al., *Oncogene*, 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.*, 14:737-744 (1996)). Trastuzumab received marketing approval from the Food and Drug Administration Sep. 25, 1998 for the treatment of patients with metastatic breast cancer whose tumors overexpress the HER2 protein. Trastuzumab is indicated for weekly treatment of patients both as first-line therapy in combination with paclitaxel and as a single agent in second- and third-line therapy.

In clinical trials, HERCEPTIN® has shown a survival benefit when used in combination with chemotherapy in metastatic breast cancer patients. In December 2001, Genentech received FDA approval to include data that showed a 24 percent increase in median overall survival for women with HER2-positive metastatic breast cancer treated initially with HERCEPTIN® and chemotherapy compared to chemotherapy alone (median 25.1 months compared to 20.3 months).

HERCEPTIN® has been used in combination with various chemotherapeutic agents, including taxoids such as paclitaxel (Slamon et al., *N. Engl. J. of Med,* 344:783-792 (2001); Leyland-Jones et al., *J. Clin. Oncol.,* 21(21):3965-3971 (2003)), and docetaxel (Esteva et at, *J. Clin. Oncol.,* 20(7): 1800-1808 (2002); (Extra et al., *Breast Cancer Res Treat,* 82 (Suppl 1):217 (2003)); taxoids and platinum compounds (Pegram et al., *J. Natl. Cancer Inst.,* 96(10):759-69 (2004); Yardley et al., *Breast Cancer Res Treat,* 76:S113 abstract 439 (2002)); platinum compound (such as cisplatin or carboplatin) (Robert et al., *Ann. Oncol.,* 15(suppl 3):39 (abstract 144P); (2004); Pegram et al., *J Clin Oncol,* 16:2659-71 (1998)); vincas such as vinorelbine (NAVELBINE®) (Burstein et al., *J. Clin. Oncol.,* 19(10); 2722-2730 (2001)); aromatase inhibitors such as letrozole and anastrazole (Jones, A., *Annals of Oncology,* 14:1697-1794 (2003); Wong et al., *Breast Cancer Res Treat,* 82(Suppl 1):444 (2003)); anti-estrogen such as fulvestrant (FASLODEX®) (Jones, A., supra); gemcitabine (GEMZAR®) (Miller et al., *Oncology,* 15(2): 38-40 (2001); O'Shaughnessy et al., *Breast Cancer Res Treat,* 69:302 abstract 523 (2001)); liposomal doxorubicin (Theodoulou et al., *Proc Am Soc Clin Oncol,* 21:216 abstract 216 (2002)); docetaxel/vinorelbine (with G-CSF and quinolone prophylaxis) Limentani et al., *Breast Cancer Res Treat,* 76:abstract 162 (2002)); epirubicin and cyclophosphomide (Untch et al., *Eur. J. Cancer,* 40: 988-97 (2004b). See also Pegram et al., *J. Natl. Cancer. Inst.,* 96(10):739-49 (2004) for various combination therapies including trastuzumab.

Other references describing Trastuzumab clinical trials include Bendell et al., *Cancer,* 97:2972-7 (2003); Clayton et al., *Brit. J. Cancer,* 91:639-43 (2004); Seidman et al., *J. Clin. Oncol.,* 20:1215-21 (2002); and Ewer et al., *Proc. Am. Soc. Clin. Oncol.,* (abstr. 489) (2002).

Other HER2 antibodies with various properties have been described in Tagliabue et al., *Int. J. Cancer,* 47:933-937 (1991); McKenzie et al., *Oncogene,* 4:543-548 (1989); Maier et al., *Cancer Res.,* 51:5361-5369 (1991); Bacus et al., *Molecular Carcinogenesis,* 3:350-362 (1990); Stancovski et al., *PNAS* (USA), 88:8691-8695 (1991); Bacus et al., *Cancer Research,* 52:2580-2589 (1992); Xu et al., *Int. J. Cancer,* 53:401-408 (1993); WO94/00136; Kasprzyk et al., *Cancer Research,* 52:2771-2776 (1992); Hancock et al., *Cancer Res.,* 51:4575-4580 (1991); Shawver et al., *Cancer Res.,* 54:1367-1373 (1994); Arteaga et al., *Cancer Res.,* 54:3758-3765 (1994); Harwerth et al., *J. Biol. Chem.,* 267:15160-15167 (1992); U.S. Pat. No. 5,783,186; and Klapper et al., *Oncogene,* 14:2099-2109 (1997).

Homology screening has resulted in the identification of two other HER receptor family members; HER3 (U.S. Pat. Nos. 5,183,884 and 5,480,968 as well as Kraus et al., *PNAS* (USA), 86:9193-9197 (1989)) and HER4 (EP patent application Ser. No. 599,274; Plowman et al., *Proc. Natl. Acad. Sci. USA,* 90:1746-1750 (1993); and Plowman et al., *Nature,* 366: 473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al., *Breast Cancer Research and Treatment,* 35:115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al., *Growth. Factors,* 11:235-257 (1994)). A family of heregulin proteins resulting from alternative splicing of a single gene are ligands for HER3 and HER4. The heregulin family includes alpha, beta and gamma heregulins (Holmes et al., *Science,* 256:1205-1210 (1992); U.S. Pat. No. 5,641,869; and Schaefer et al., *Oncogene,* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al., *Growth Factors,* 11:235-257 (1994); Lemke, G., *Molec. & Cell. Neurosci.,* 7:247-262 (1996) and Lee et al., *Pharm. Rev.,* 47:51-85 (1995). Recently three additional HER ligands were identified; neuregulin-2 (NRG-2) which is reported to bind either HER3 or HER4 (Chang et al., *Nature,* 387 509-512 (1997); and Carraway et al., *Nature,* 387:512-516 (1997)); neuregulin-3 which binds HER4 (Zhang et al., *PNAS* (USA), 94(18):9562-7 (1997)); and neuregulin-4 which binds HER4 (Harari et al., *Oncogene,* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.,* 269(20):14661-14665 (1994)). Additionally, the affinity of HER3 for heregulin (HRG) is increased to a higher affinity state when co-expressed with HER2. See also, Levi et al., *Journal of Neuroscience,* 15: 1329-1340 (1995); Morrissey et al., *Proc. Natl. Acad. Sci. USA,* 92:1431-1435 (1995); and Lewis et al., *Cancer Res.,* 56:1457-1465 (1996) with respect to the HER2-HER3 protein complex. HER4, like HER3, forms an active signaling complex with HER2 (Carraway and Cantley, *Cell,* 78:5-8 (1994)).

Patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat. Nos. 5,648,237, 6,267,958, 6,685,940, 6,821,515, WO98/17797, U.S. Pat. Nos. 6,127,526, 6,333,398, 6,797,814, 6,339,142, 6,417,335, 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. Nos. 6,627,196B1, 6,632,979B1, WO01/00244, US2002/0090662A1, WO01/89500, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. Nos. 5,985,553, 5,747,261, 4,935,341, 5,401,638, 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. Nos. 5,571,894, 5,939,531, EP 502,812 B1, WO 93/03741, EP 554,441 B1, EP 656,367 A1, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028,059, WO 96/07321, U.S. Pat. Nos. 5,804,396, 5,846,749, EP 711,565, WO 96/16673, U.S. Pat. Nos. 5,783,404, 5,977,322, 6,512,097, WO 97/00271, U.S. Pat. Nos. 6,270,765, 6,395,272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

Patients treated with the HER2 antibody trastuzumab may be selected for therapy based on HER2 overexpression/amplification. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, US2003/0152987, Cohen et al., concerning immunohistochemistry (IHC) and fluorescence in situ hybridization (FISH) for detecting HER2 overexpression and amplification.

WO2004/053497 and US2004/024815A1 (Bacus et al.), as well as US 2003/0190689 (Crosby and Smith), refer to determining or predicting response to trastuzumab therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290, Cobleigh et al., concerns gene expression markers for breast cancer prognosis.

Patients treated with pertuzumab can be selected for therapy based on HER activation or dimerization. Patent publications concerning pertuzumab and selection of patients for therapy therewith include: WO01/00245 (Adams et al.); US2003/0086924 (Sliwkowski, M.); US2004/0013667A1 (Sliwkowski, M.); as well as WO2004/008099A2, and US2004/0106161 (Bossenmaier et al.).

Cronin et al., *Am. J. Path.*, 164(1):35-42 (2004) describes measurement of gene expression in archival paraffin-embedded tissues. Ma et al., *Cancer Cell*, 5:607-616 (2004) describes gene profiling by gene oliogonucleotide microarray using isolated RNA from tumor-tissue sections taken from archived primary biopsies.

Adjuvant Therapy

Adjuvant therapy, in the broadest sense, is treatment given in addition to the primary therapy to kill any cancer cells that may have spread, even if the spread cannot be detected by radiologic or laboratory tests. Contemporary clinical trials have evaluated the efficacy of chemotherapeutic agents for breast cancer adjuvant therapy, namely BCIRG 001 (comparing paclitaxel, doxorubicin, and cyclophosphomide (TAC) to fluorouracil, doxorubicin, and cyclophosphomide FAC); CALGB 9741 (dose dense tiral); and CALGC 9344 (anthracycline+cyclosphosphomide (AC) compared to AC+paclitaxel (AC/T)).

In the BCRIG 001 trial, the disease free survival (DFS) hazard ratio was 0.72 (p=0.0010), 5 year DFS for TAC was 75%, and for FAC was 68%. Overal survival (OS) hazard ratio was 0.70 (p=0.0080), 5 year OS for TAC was 87%, and for FAC was 81%. For HER2 positive (HER2+) subjects (n=328) in this trial, DFS hazard ratio was 0.60 (p=0.0088).

CALGB 9741 was a dose dense trial comparing AC×4 to T×4; sequential A×4 to T×4 to C×4; dose dense sequential A×4 to T×4 to C×4; and dose dense AC×4 to T×4 (A=anthracycline; C=cyclophosphomide; T=paclitaxel). DFS hazard ratio (dose dense versus standard) was 0.74 (p=0.010); 4 year DFS was 82% versus 75%. OS hazard ratio (dose dense versus standard) was 0.69 (p=0.013).

CALGB 9344 compared the efficacy of AC to AC/T. DFS hazard ratio was 0.83 (p=0.002), with 5 year DFS of 65% for AC and 70% for AC/T. OS hazard ratio was 0.82 (p=0.0064), with 5 year OS for AC of 77% and for AC/T of 80%.

According to the American Cancer Society, an estimated 211,000 women will be diagnosed with breast cancer and approximately 40,000 women will die of the disease in the United States in 2005. Breast cancer is the most common cause of cancer among women in the United States and a woman is diagnosed with breast cancer in the United States every three minutes. About 30% of women diagnosed with breast cancer will have lymph node-positive breast cancer.

Publications or seminars related to adjuvant therapy include: Paik et al., *J. Natl. Cancer Inst.*, 92(24):1991-1998 (2000); Paik et al., *J. Natl. Cancer Inst.*, 94:852-854 (2002); Paik et al. Successful quality assurance program for HER2 testing in the NSABP Trial for Herceptin. *San Antonio Breast Cancer Symposium*, 2002; Roche P C et al., *J. Natl. Cancer Inst.*, 94(11):855-7 (2002); Albain et al., *Proceedings of the American Society of Clinical Oncology Thirty-Eighth Annual Meeting*, May 18-21 2002, Orlando, Fla., Abstract 143; The ATAC (Arimidex, Tamoxifen Alone or in Combination) Trialists' Group, *Lancet*, 359:2131-39 (2002); Geyer et al., *26th Annual San Antonio Breast Cancer Symposium (SABCS)*, December 2003, Abstract 12; Perez et al., *Proc. ASCO*, 2005, Abstract 556.

U.S. Patent Publication No. 2004/0014694 (published Jan. 22, 2004) describes a method of adjuvant therapy for the treatment of early breast cancer, comprising administration of docetaxel, doxorubicin and cyclophosphamide.

SUMMARY OF THE INVENTION

The invention herein concerns the results obtained in clinical studies of the adjuvant use of HERCEPTIN® in human subjects with nonmetastatic, high risk, breast cancer. The efficacy, as evaluated by disease free survival (DFS) and overall survival (OS) was remarkable, especially when compared to DFS and OS data for chemotherapeutic agents recently tested in clinical trials for use in the adjuvant setting. Surprisingly, subjects in the clinical trials who received HERCEPTIN® in combination with paclitaxel, following anthracycline (doxorubicin)/cyclophosphamide (AC) chemotherapy, had a 52% decrease in disease recurrence (first breast cancer event) compared to subjects treated with AC followed by paclitaxel alone at 3 years. The difference was highly significant.

The results were particularly impressive and surprising, given that the subjects were HER2 positive, and therefore at high risk for recurrence, since HER2 amplification or overexpression has been linked with more aggressive disease and greater risk of recurrence. In addition, aside from their HER2 positivity, the subjects included in, the trials were selected by criteria that further increased their risk for recurring, including the number of involved lymph nodes, size of the primary tumor, etc. The significant improvement over chemotherapy alone, is particularly unexpected in such subjects.

This invention constitutes a significant medical breakthrough providing for the more effective care of subjects with nonmetastatic breast cancer.

In one aspect, the invention concerns a method of adjuvant therapy comprising administering to a human subject with nonmetastatic HER2 positive breast cancer, following definitive surgery, an effective amount of an antibody which binds to HER2 Domain IV bound by trastuzumab (HERCEPTIN®) and at least one chemotherapeutic agent, so as to extend disease free survival (DFS) or overall survival (OS) in the subject, wherein the DFS or the OS is evaluated about 2 to 5 years after initiation of treatment.

In another aspect, the invention concerns a method of curing nonmetastatic breast cancer in a population of human subjects with nonmetastatic HER2 positive breast cancer comprising administering an effective amount of trastuzumab (HERCEPTIN®) and taxoid to the population of subjects following definitive surgery, and evaluating the population of subjects after about four years to confirm no disease recurrence has occurred in at least about 80% of the population.

In yet another aspect, the invention concerns a method of decreasing disease recurrence in a population of human subjects with nonmetastatic HER2 positive breast cancer comprising administering an effective amount of trastuzumab (HERCEPTIN®) and taxoid to the subjects following definitive surgery, wherein disease recurrence at about 3 years is decreased by at least about 50% compared to subjects treated with taxoid alone.

In a particular embodiment of these methods, the administration of the antibody and chemotherapeutic agent decreases disease cancer recurrence in a population of subjects by about 50% compared to subjects treated with chemotherapy, such as anthacycline/cyclophosphamide followed by paclitaxel, alone. In another embodiment, the subject has a high risk of cancer recurrence. In another embodiment, the population comprises 3000 or more human subjects.

In a further aspect, the invention concerns a method of adjuvant therapy comprising administering to a human subject with nonmetastatic HER2 positive breast cancer, following definitive surgery, an antibody which binds to HER2 Domain IV bound by trastuzumab (HERCEPTIN®) and at least one chemotherapeutic agent, in an amount effective to extend disease free survival (DFS) or overall survival (OS), relative to standard of care chemotherapy, wherein the DFS or the OS is evaluated at least once a year for at least about 3 years after initiation of treatment, wherein DFS is extended if the patient remains alive, without cancer recurrence for at least one year, and OS is extended if the patient remains alive for at least one year, from initiation of treatment.

In a still further aspect, the invention concerns a method of instructing a human subject with non-metastatic HER2 positive breast cancer identified as having a high risk of cancer recurrence or low likelihood of survival following definitive surgery, and who is being treated solely by standard of care chemotherapy to receive treatment with an antibody which binds to HER2 Domain IV bound by trastuzumab (HERCEPTIN®) and at least one chemotherapeutic agent.

In a different aspect, the invention concerns a promotional method, comprising promoting, for the treatment of HER2 positive nonmetastatic breast cancer in human subjects identified as being at high risk of cancer recurrence or low likelihood of survival following definitive surgery: (a) a chemotherapeutic agent in combination with an antibody which binds to HER2 Domain IV bound by trastuzumab (HERCEPTIN®); or (b) an antibody which binds to HER2 Domain IV bound by trastuzumab (HERCEPTIN®) in combination with a chemotherapeutic agent.

In yet another aspect, the invention concerns a business method, comprising marketing a chemotherapeutic agent for treating HER2 positive nonmetastatic breast cancer in human subjects identified as being at high risk of cancer recurrence or low likelihood of survival following definitive surgery in combination with an antibody which binds to HER2 Domain IV bound by trastuzumab (HERCEPTIN®), so as to decrease the subjects' likelihood of cancer recurrence or increase the subjects' likelihood of survival.

In a further aspect, the invention concerns a business method, comprising marketing an antibody which binds to HER2 Domain IV bound by trastuzumab (HERCEPTIN®) for treating HER2 positive nonmetastatic breast cancer in human subjects identified as being at high risk of cancer recurrence or low likelihood of survival following definitive surgery in combination with a chemotherapeutic agent, so as to decrease the subjects' likelihood of cancer recurrence or increase the subjects' likelihood of survival.

The invention also concerns a method of adjuvant therapy comprising administering to a human subject with nonmetastatic HER2 positive breast cancer, following definitive surgery, an antibody which binds to HER2 Domain IV bound by trastuzumab (HERCEPTIN®), as a single agent, in an amount effective to extend disease free survival (DFS) or overall survival (OS), wherein the DFS or the OS is confirmed at least about one year after an initial administration of the antibody.

In all aspects, a preferred antibody blocks binding of trastuzumab (HERCEPTIN®) to HER2. More preferably, the antibody comprises trastuzumab (HERCEPTIN®). The chemotherapeutic agent can be selected, without limitation, from the group consisting of taxoid, vinca, platinum compound, aromatase inhibitor, anti-estrogen, etoposide, thiotepa, cyclophosphamide, methotrexate, liposomal doxorubicin, pegylated liposomal doxorubicin, capecitabine, and gemcitabine. In a preferred embodiment, the chemotherapeutic agent is a taxoid, such as, for example, paclitaxel or docetaxel, most preferably paclitaxel.

In all aspects, preferably the chemotherapeutic agent, such a taxoid, and the antibody are administered concurrently.

In all aspects, the chemotherapeutic agent, such as taxoid, and the antibody are preferably administered following other standard chemotherapy, administered post-operation. In a preferred embodiment, the standard chemotherapy is the administration of anthracycline (doxorubicin) and cyclophosphamide.

In all aspects, the subject is preferably relatively young, e.g., less than about 50 years, or less than about 45 years, or less than about 40 years old.

In all aspects, the methods include treatment of subjects having a tumor greater than 2 centimeters in diameter, and/or subjects with lymph node-positive cancer (having 4-9, or 10 or more involved lymph nodes), and/or estrogen receptor (ER) negative subjects, and/or progesterone receptor (PG) negative subjects.

In all aspects, the antibody can, for example, be an intact, naked antibody.

In a particular embodiment, DFS or OS is evaluated 5 years after initiation of treatment.

In a further embodiment, administration of the antibody and chemotherapeutic agent decreases disease recurrence in a population of subjects by about 50% compared to subjects treated with the chemotherapteutic agent, without the antibody.

BRIEF DESCRIPTION OF THE DRAWINGS

Figure 2A:
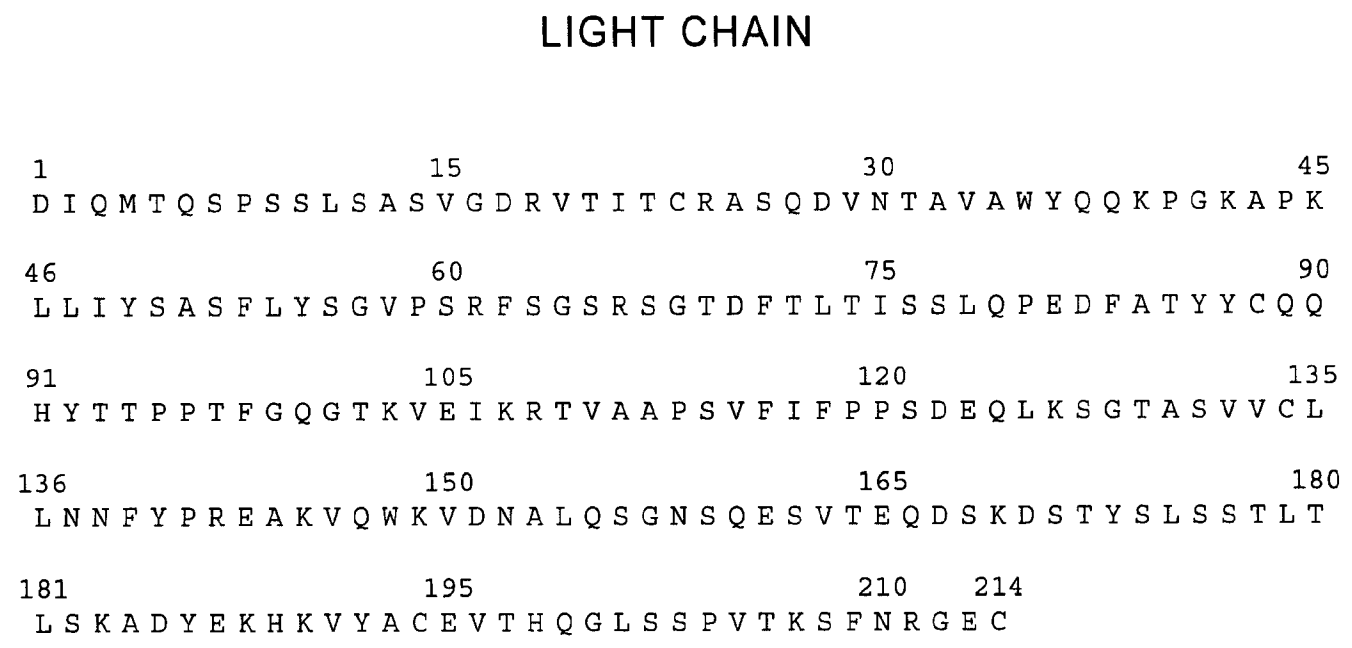

FIGS. 2A and 2B show the amino acid sequences of trastuzumab light chain (FIG. 2A; SEQ ID NO: 5) and heavy chain (FIG. 2B: SEQ ID No: 6), respectively.

FIG. 4A depicts the study design for the NSABP B-31 and NCCTG N9831 (Intergroup) studies, respectively.

FIG. 5 depicts patient and tumor characteristics for the AC→paclitaxel and AC→paclitaxel+trastuzumab arms of the B-31 and N9831 studies. The results are grouped by the age of patients, number of positive lymph nodes, hormone receptor status, and tumor size.

FIG. 12 is a summary of efficacy endpoint analyses.

Figure 14A:
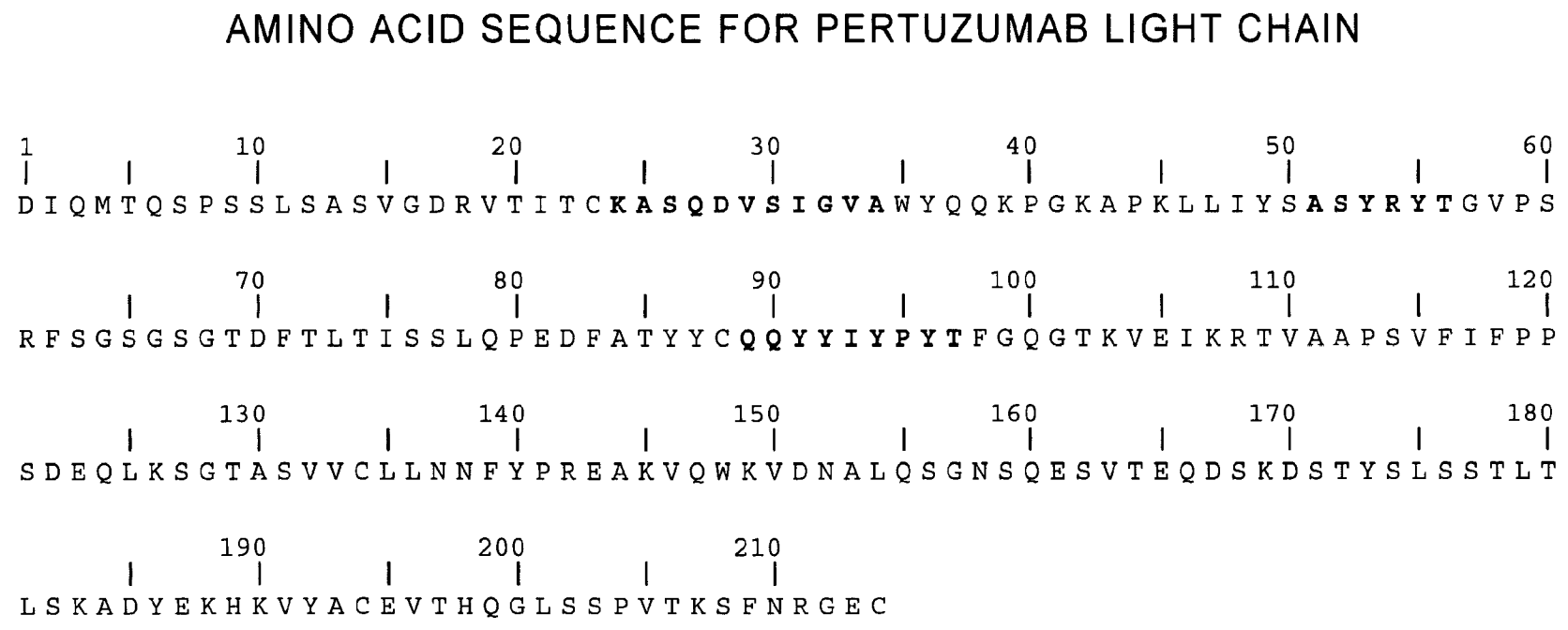

FIGS. 14A and 14B show the amino acid sequences of pertuzumab light chain (FIG. 14A; SEQ ID NO: 7) and heavy chain (FIG. 14B; SEQ ID NO: 8). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

DETAILED DESCRIPTION OF THE PREFERRED EMBODIMENTS

I. Definitions

Figure 1:
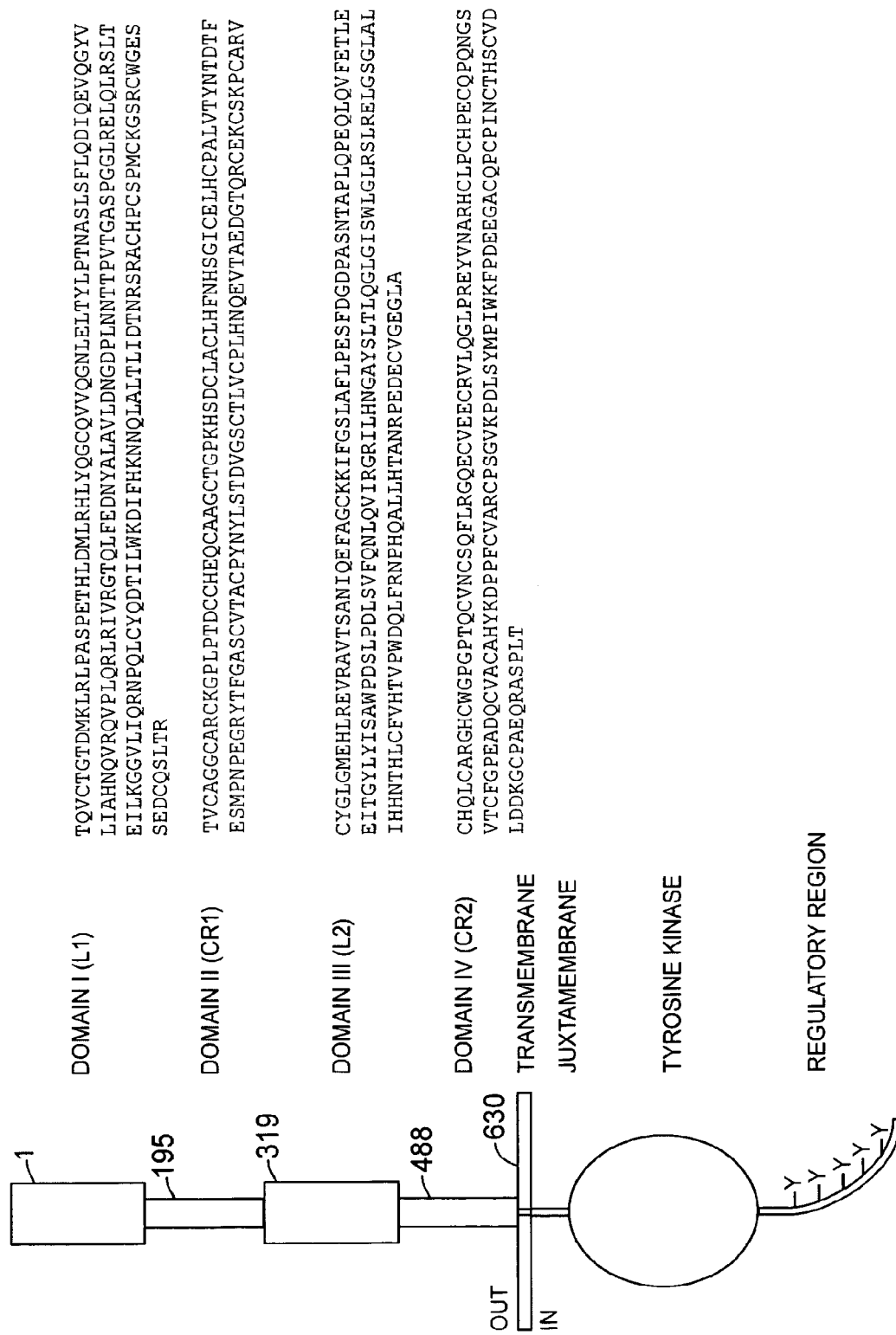
FIG. 1 provides a schematic of the HER2 protein structure, and amino acid sequences for Domains I-IV (SEQ ID NOS: 1-4, respectively) of the extracellular domain thereof.
Figure 3:
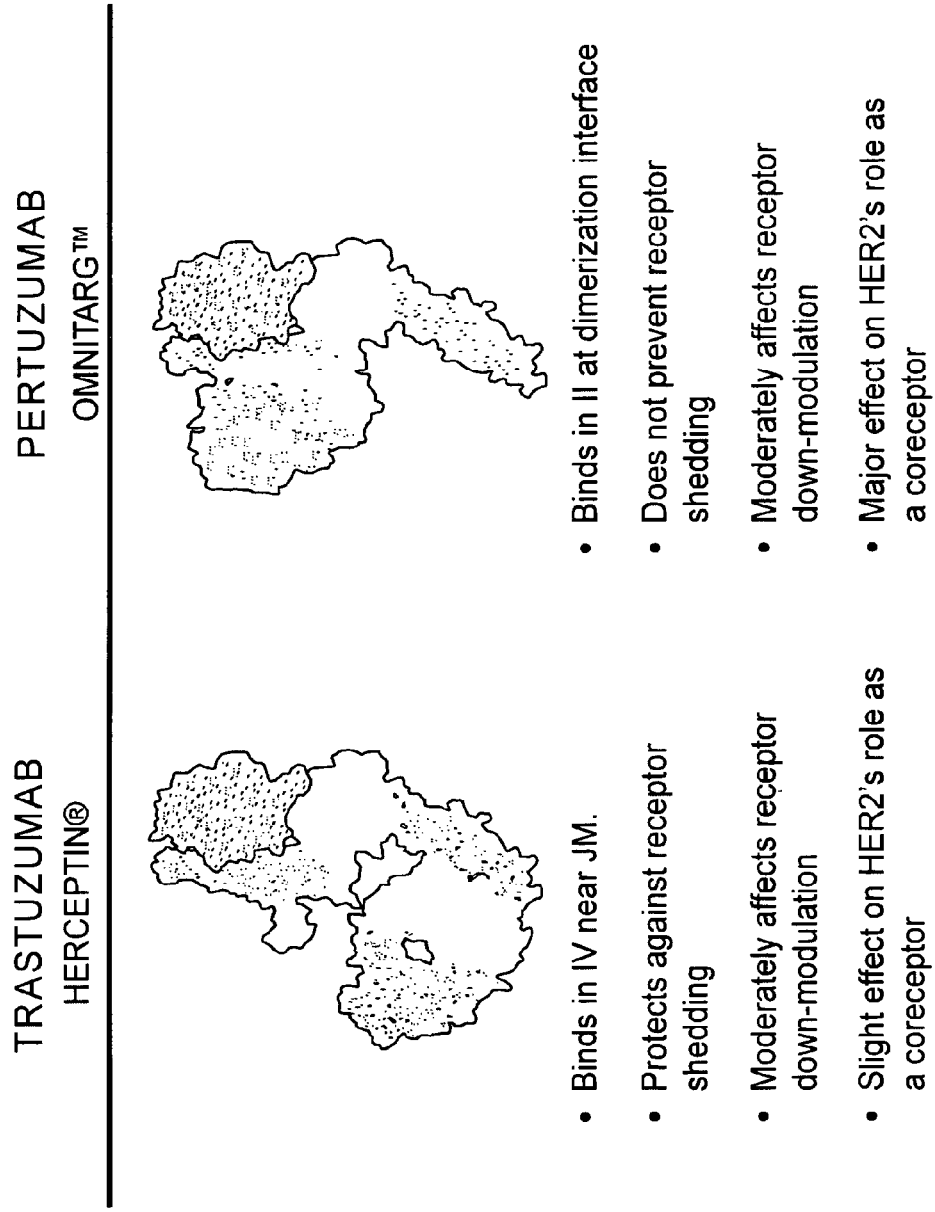
FIG. 3 depicts differences between functions of two different HER2 antibodies; trastuzumab and pertuzumab.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy, e.g., where the subject is treated with a chermotherapeutic agent and/or HERCEPTIN®, prior to definitive surgery.

"Definitive surgery" refers to complete removal of tumor and surrounding tissue as well as any involved lymph nodes. Such surgery includes lumpectomy, mastectomy, such as total mastectomy plus axillary dissection, double mastectomy etc.

"Breast cancer" herein refers to cancer involving breast cells or tissue.

"Metastatic" breast cancer refers to cancer which has spread to parts of the body other than the breast and the regional lymph nodes.

"Nonmetastatic" breast cancer is cancer which is confined to the breast and/or regional lymph nodes.

"Survival" refers to the patient remaining alive, and includes disease free survival (DFS) as well as overall survival (OS).

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In the studies underlying the present invention, DFS was analyzed according to the intent-to-treat principle, ie, patients were evaluated on the basis of their assigned therapy. The events used in the analysis of DFS included local, regional and distant recurrence of cancer, occurrence of secondary cancer, death from any cause in patients without a prior event (breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis. In the studies underlying the present invention the event used for survival analysis was death from any cause.

The term "effective amount" refers to an amount of a drug or drug combination effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may improve disease free survival (DFS), improve overall survival (OS), decrease likelihood of recurrence, extend time to recurrence, extend time to distant recurrence (i.e., recurrence outside of the breast), cure cancer, improve symptoms of breast cancer (e.g., as gauged using a breast cancer specific survey), reduce contralateral breast cancer, reduce appearance of second primary cancer, etc.

By "extending survival" is meant increasing DFS and/or OS in a treated patient relative to an untreated patient (i.e., relative to a patient not treated with the HER2 antibody, HERCEPTIN®), or relative to a control treatment protocol, such as treatment only with the chemotherapeutic agent, such as paclitaxel. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

"Hazard ratio" in survival analysis is a summary of the difference between two survival curves, representing the reduction in the risk of death on treatment compared to control, over a period of follow-up. Hazard ratio is a statistical definition for rates of events. For the purpose of the present invention, hazard ratio is defined as representing the probability of an event in the experimental arm divided by the probability of an event in the control arm at any specific point in time.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

For the methods of the present invention, the term "instructing" a subject means providing directions for applicable therapy, medication, treatment, treatment regimens, and the like, by any means, but preferably in writing, such as in the form of package inserts or other written promotional material.

For the methods of the present invention, the term "promoting" means offering, advertising, selling, or describing a particular drug, combination of drugs, or treatment modality, by any means, including writing, such as in the form of package inserts. Promoting herein refers to promotion of a therapeutic agent, such as a HER2 antibody or chemotherapeutic agent, for an indication, such as adjuvant breast cancer, where such promoting is authorized by the Food and Drug Administration (FDA) as having been demonstrated to be associated with statistically significant therapeutic efficacy and acceptable safety in a population of subjects.

The term "marketing" is used herein to describe the promotion, selling or distribution of a product (e.g., drug). Marketing specifically includes packaging, advertising, and any business activity with the purpose of commercializing a product.

A "subject" herein is a human subject.

A "population" of subjects refers to a group of subjects with breast cancer, such as in a clinical trial, or as seen by oncologists following FDA approval for a particular indication, such as breast cancer adjuvant therapy. In one embodiment, the population comprises at least 3000 subjects.

"Node-positive breast cancer" is breast cancer that has spread to the regional lymph nodes (usually those under the arm). Subjects with node-positive breast cancer herein included those with 1-3 involved nodes; 4-9 involved nodes; and 10 or more involved nodes. Subjects with 4 or more involved nodes are at higher risk of recurrence than those with less or no involved nodes.

"Cancer recurrence" herein refers to a return of cancer following treatment, and includes return of cancer in the breast, as well as distant recurrence, where the cancer returns outside of the breast.

A subject at "high risk of cancer recurrence" is one who has a greater chance of experiencing recurrence of cancer, for example, relatively young subjects (e.g., less than about 50 years old), those with positive lymph nodes, particularly 4 or more involved lymph nodes (including 4-9 involved lymph nodes, and 10 or more involved lymph nodes), those with tumors greater than 2 cm in diameter, those with HER2-positive breast cancer, and those with hormone receptor negative breast cancer (i.e., estrogen receptor (ER) negative and progesterone receptor (PR) negative). A subject's risk level can be determined by a skilled physician. Generally, such high risk subjects will have lymph node involvement (for example with 4 or more involved lymph nodes); however, subjects without lymph node involvement are also high risk, for example if their tumor is greater or equal to 2 cm.

"Estrogen receptor (ER) positive" cancer is cancer which tests positive for expression of ER. Conversely, "ER negative" cancer tests negative for such expression. Analysis of ER status can be performed by any method known in the art. For the purpose of the studies herein, ER-positive tumors are defined as ≥10 fmol/mg cytosol protein by the Dextran-coated charcoal or sucrose-density gradient method, or positive (using individual laboratory criteria) by the enzyme immunoassay (EIA) method, or by immunocytochemical assay.

"Progesterone receptor (PR) positive" cancer is cancer which tests positive for expression of PR. Conversely, "PR negative" cancer tests negative for such expression. Analysis of PR status can be performed by any method known in the art. For the purpose of the studies herein, acceptable methods include the Dextran-coated charcoal or sucrose-density gradient methods, enzyme immunoassay (EIA) techniques, and immunocytochemical assays.

Herein, "initiation of treatment" refers to the start of a treatment regimen following surgical removal of the tumor. In one embodiment, such may refer to administration of AC following surgery. Alternatively, this can refer to an initial administration of the HER2 antibody and/or chemotherapeutic agent.

By an "initial administration" of a HER2 antibody and chemotherapeutic agent is meant a first dose of the HER2 antibody or chemotherapeutic agent as part of a treatment schedule.

By "curing" cancer herein is meant the absence of cancer recurrence at about 4 or about 5 years after beginning adjuvant therapy.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a Anative sequence@ HER receptor or an Aamino acid sequence variant@ thereof. Preferably the HER receptor is native sequence human HER receptor.

"HER activation" refers to activation, or phosphorylation, of any one or more HER receptors. Generally, HER activation results in signal transduction (e.g., that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

The expressions "ErbB2" and "HER2" are used interchangeably herein and refer to human HER2 protein described, for example, in Semba et al., *PNAS* (USA), 82:6497-6501 (1985) and Yamamoto et al., *Nature,* 319:230-234 (1986) (Genebank accession number X03363). The term "AerbB2" refers to the gene encoding human ErbB2 and Aneu@ refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. In one embodiment, the extracellular domain of HER2 may comprise four domains: ADomain I@ (amino acid residues from about 1-195; SEQ ID NO: 1), ADomain II@ (amino acid residues from about 196-319; SEQ ID NO: 2), ADomain III@ (amino acid residues from about 320-488: SEQ ID NO: 3), and ADomain IV@ (amino acid residues from about 489-630; SEQ ID NO: 4) (residue numbering without signal peptide). See Garrett et al., *Mol. Cell.,* 11: 495-505 (2003), Cho et al., *Nature,* 421:756-760 (2003), Franklin et al., *Cancer Cell,* 5:317-328 (2004), and Plowman et al., *Proc. Natl. Acad. Sci.,* 90:1746-1750 (1993), as well as FIG. 1 herein.

An antibody which "binds to HER2 Domain IV bound by trastuzumab (HERCEPTIN®)" binds to an epitope comprising or including residues from about 489-630 (SEQ ID NO:4) of HER2 ECD. The preferred such antibody is trastuzumab, or an affinity matured variant thereof, and/or comprising a variant Fc region (for instance with improved effector function).

An antibody which "blocks binding of trastuzumab (HERCEPTIN®) to HER2" is one which can be demonstrated to block trastuzumab's binding to HER2, or compete with trastuzumab for binding to HER2. Such antibodies may be identified using cross-blocking assays such as those described in *Antibodies, A Laboratory Manual,* Cold Spring Harbor Laboratory, Ed Harlow and David Lane (1988); or Fendly et al., *Cancer Research,* 50:1550-1558 (1990), for example.

The "trastuzumab (HERCEPTIN®) epitope" herein is the region in the extracellular domain of HER2 to which the antibody 4D5 (ATCC CRL 10463) or trastuzumab bind. This epitope is close to the transmembrane domain of HER2, and within Domain IV of HER2. To screen for antibodies which bind to this epitope, a cross-blocking assay such as that described in *Antibodies, A Laboratory Manual,* Cold Spring Harbor Laboratory, Ed Harlow and David Lane (1988) or Fendly et al., *Cancer Research,* 50:1550-1558 (1990), can be performed. Alternatively, epitope mapping can be performed to assess whether the antibody binds to the Trastuzumab epitope of HER2 (e.g., any one or more residues in the region from about residue 529 to about residue 625, inclusive of the HER2 ECD, residue numbering including signal peptide). One can also study the antibody-HER2 structure (Franklin et al., *Cancer Cell,* 5:317-328 (2004)) to see what epitope of HER2 is bound by the antibody.

For the purposes herein, "trastuzumab," "HERCEPTIN®" and "huMAb4D5-8" refer to an antibody comprising the light and heavy chain amino acid sequences in SEQ ID NOS: 5 and 6, respectively.

For the purposes herein, a "HER2 positive" cancer or tumor is one which expresses HER2 at a level which exceeds the level found on normal breast cells or tissue. Such HER2 positivity may be caused by HER2 gene amplification, and/or increased transcription and/or translation. HER2 positive tumors can be identified in various ways, for instance, by evaluating protein expression/overexpression (e.g., using the DAKO HERCEPTEST®) immunohistochemistry assay, by evaluating HER2 nucleic acid in the cell (for example via fluorescent in situ hybridization (FISH), see WO98/45479 published October, 1998, including as the Vysis PATHVISION® FISH assay; southern blotting; or polymerase chain reaction (PCR) techniques, including quantitative real time PCR (qRT-PCR)), by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods,* 132:73-80 (1990)), or by exposing cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody. Moreover, HER2 positive cancer or tumor samples can be identified indirectly, for instance by evaluating downstream signaling mediated through HER2 receptor, gene expression profiling etc.

The terms "ErbB1," "HER1", "epidermal growth factor receptor" and "EGFR" are used interchangeably herein and refer to EGFR as disclosed, for example, in Carpenter et al., *Ann. Rev. Biochem.,* 56:881-914 (1987), including naturally occurring mutant forms thereof (e.g., a deletion mutant EGFR as in Humphrey et al., *PNAS* (USA), 87:4207-4211 (1990)). erbB1 refers to the gene encoding the EGFR protein product.

"AErbB3" and "AHER3" refer to the receptor polypeptide as disclosed, for example, in U.S. Pat. Nos. 5,183,884 and 5,480,968 as well as Kraus et al., *PNAS* (USA), 86:9193-9197 (1989).

The terms "ErbB4" and "AHER4" herein refer to the receptor polypeptide as disclosed, for example, in EP patent application Ser. No. 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.,* 247:7612-7621 (1972)); transforming growth factor alpha (TGF-α) (Marquardt et al., *Science,* 223:1079-1082 (1984)); amphiregulin also known as schwanoma or keratinocyte autocrine growth factor (Shoyab et al., *Science,* 243:1074-1076 (1989); Kimura et al., *Nature,* 348:257-260 (1990); and Cook et al., *Mol. Cell. Biol.,* 11:2547-2557 (1991)); betacellulin (Shing et al., *Science,* 259:1604-1607 (1993); and Sasada et al., *Biochem. Biophys. Res. Commun.,* 190:1173 (1993)); heparin-binding epidermal growth factor (HB-EGF) (Higashiyama et al., *Science,* 251:936-939 (1991)); epiregulin (Toyoda et al., *J. Biol. Chem.,* 270:7495-7500 (1995); and Komurasaki et al., *Oncogene,* 15:2841-2848 (1997)); a heregulin (see below); neuregulin-2 (NRG-2) (Carraway et al., *Nature,* 387:512-516 (1997)); neuregulin-3 (NRG-3) (Zhang et al., *Proc. Natl. Acad. Sci.,* 94:9562-9567 (1997)); neuregulin-4 (NRG-4) (Harari et al., *Oncogene,* 18:2681-89 (1999)); and cripto (CR-1) (Kannan et al., *J. Biol. Chem.,* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362: 312-318 (1993). Examples of heregulins include heregulin-α, heregulin-β1, heregulin-β2 and heregulin-β3 (Holmes et al., Science, 256:1205-1210 (1992); and U.S. Pat. No. 5,641,869); neu differentiation factor (NDF) (Peles et al., Cell, 69: 205-216 (1992)); acetylcholine receptor-inducing activity (ARIA) (Falls et al., Cell, 72:801-815 (1993)); glial growth factors (GGFs) (Marchionni et al., Nature, 362:312-318 (1993)); sensory and motor neuron derived factor (SMDF) (Ho et al., J. Biol. Chem., 270:14523-14532 (1995)); γ-heregulin (Schaefer et al., Oncogene, 15:1385-1394 (1997)).

A "HER dimmer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., J. Biol. Chem., 269(20): 14661-14665 (1994), for example. Other proteins, such as a cytokine receptor subunit (e.g., gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER inhibitor" is an agent which interferes with HER activation or function. Examples of HER inhibitors include HER antibodies (e.g., EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Akt. Preferably, the HER inhibitor is an antibody or small molecule which binds to a HER receptor.

A "HER2 heterodimerization inhibitor" is an agent which inhibits formation of a heterodimer comprising HER2. Preferably, the HER2 heterodimerization inhibitor is an antibody, for example an antibody which binds to HER2 at the heterodimeric binding site thereof. The most preferred HER2 heterodimerization inhibitor herein is pertuzumab or MAb 2C4. Other examples of HER2 heterodimerization inhibitors include antibodies which bind to EGFR and inhibit dimerization thereof with HER2 (for example EGFR monoclonal antibody 806, MAb 806, which binds to activated or "untethered" EGFR; see Johns et al., J. Biol. Chem., 279(29):30375-30384 (2004)); antibodies which bind to HER3 and inhibit dimerization thereof with HER2; antibodies which bind to HER4 and inhibit dimerization thereof with HER2; peptide dimerization inhibitors (U.S. Pat. No. 6,417,168); antisense dimerization inhibitors; etc.

A HER2 antibody that Abinds to a heterodimeric binding site@ of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al., Cancer Cell, 5:317-328 (2004) characterize the HER2-pertuzumab crystal structure, deposited with the RCSB Protein Data Bank (ID Code IS78), illustrating an exemplary antibody that binds to the heterodimeric binding site of HER2.

Protein "expression" refers to conversion of the information encoded in a gene into messenger RNA (mRNA) and then to the protein.

Herein, a sample or cell that "expresses" a protein of interest (such as HER2) is one in which mRNA encoding the protein, or the protein, including fragments thereof, is determined to be present in the sample or cell.

A "native sequence" polypeptide is one which has the same amino acid sequence as a polypeptide (e.g., HER receptor or HER ligand) derived from nature, including naturally occurring or allelic variants. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222: 581-597 (1991); Sidhu et al., J. Mol. Biol., 338(2):299-310 (2004); Lee et al., J. Mol. Biol., 340(5):1073-1093 (2004); Fellouse, Proc. Nat. Acad. Sci. USA, 101(34):12467-12472 (2004); and Lee et al., J. Immunol. Methods, 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., Bio/Technology, 10:779-783 (1992); Lonberg et al., Nature, 368: 856-859 (1994); Morrison, Nature, 368: 812-813 (1994); Fishwild et al., Nature Biotechnology, 14:845-851 (1996); Neuberger, Nature Biotechnology, 14:826 (1996); and Lonberg and Huszar, Intern. Rev. Immunol., 13:65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include Aprimatized@ antibodies comprising variable domain antigen-binding sequences derived from a non-human primate (e.g., Old World Monkey, Ape, etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature, 321:522-525 (1986); Riechmann et al., Nature, 332:323-329 (1988); and Presta, Curr. Op. Struct. Biol., 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab (HERCEPTIN7) as described in Table 3 of U.S. Pat. No. 5,821,337 expressly incorporated herein by reference; humanized 520C9 (WO93/21319); and humanized 2C4 antibodies such as pertuzumab as described herein.

Herein, Apertuzumab@ and AOMNITARGJ@ refer to an antibody comprising the light and heavy chain amino acid sequences in SEQ ID NOS: 7 and 8, respectively.

An Aintact antibody@ herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term Ahypervariable region@ when used herein refers to the amino acid residues of an antibody which are responsible for antigen-binding. The hypervariable region generally comprises amino acid residues from a Acomplementarity determining region@ or ACDR@ (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a Ahypervariable loop@ (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this Configuration that the three hypervariable regions of each variable domain interact to define an antigen-binding site on the surface of the $V_H$–$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHl) of the heavy chain. Fab=fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different Aclasses@. There are five major classes of intact antibodies: IgA, IgD, IgE, IgG, and IgM, and several of these may be further divided into Asubclasses@ (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

AAntibody-dependent cell-mediated Cytotoxicity® and AADCC@ refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol,* 9:457-92 (1991). To assess ADCC activity of a molecule of interest, an in vitro ADCC assay, such as that described in U.S. Pat. Nos. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA), 95:652-656 (1998).

A Human effector cells@ are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T-cells and neutrophils; with PBMCs and NK cells being preferred. The effector cells may be isolated from a native source thereof, e.g., from blood or PBMCs as described herein.

The terms "Fc receptor" or AFcR@ are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.,*

15:203-234 (1997)). FcRs are reviewed in Ravetch and Kinet, *Annu. Rev. Immunol*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976) and Kim et al., *J. Immunol.*, 24:249 (1994)), and regulates homeostasis of immunoglobulins.

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g. as described in Gazzano-Santoro et al., *J. Immunol. Methods*, 202:163 (1996), may be performed.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A Anaked antibody@ herein is an antibody that is not conjugated to a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology*, 10:779-783 (1992) describes affinity maturation by $V_H$ and $V_L$ domain shuffling. Random mutagenesis of CDR and/or framework residues is described by: Barbas et al., *Proc Nat. Acad. Sci, USA*, 91:3809-3813 (1994); Schier et al., *Gene*, 169:147-155 (1995); Yelton et al., *J. Immunol.*, 155:1994-2004 (1995); Jackson et al., *J. Immunol.*, 154(7):3310-9 (1995); and Hawkins et al, *J. Mol. Biol.*, 226:889-896 (1992).

The term "main species antibody" herein refers to the antibody structure in a composition which is the quantitatively predominant antibody molecule in the composition. In one embodiment, the main species antibody is a HER2 antibody, such as an antibody that binds Domain IV of HER2 ECD bound by trastuzumab (HERCEPTIN®). The preferred embodiment herein of the main species antibody is one comprising the light chain and heavy chain amino acid sequences in SEQ ID Nos. 5 and 6 (trastuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g., deamidated antibody variant), a basic variant, an antibody with a C-terminal lysine residue on one or two heavy chains thereof, etc, and includes combinations of variations to the amino acid sequences of heavy and/or light chains.

A "glycosylation variant" antibody herein is an antibody with one or more carbohydrate moeities attached thereto which differ from one or more carbohydate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc., and combinations of glycosylation alterations.

Where the antibody has an Fc region, an oligosaccharide structure may be attached to one or two heavy chains of the antibody, e.g., at residue 299 (298, Eu numbering of residues).

A "deamidated" antibody is one in which one or more asparagine residues thereof has been derivitized, e.g., to an aspartic acid, a succinimide, or an iso-aspartic acid.

A "tumor sample" herein is a sample derived from, or comprising tumor cells from, a patient=s tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

Herein, "gene expression profiling" refers to an evaluation of expression of one or more genes as a surrogate for determining HER2 receptor expression directly.

A "phospho-ELISA assay" herein is an assay in which phosphorylation of one or more HER receptors, especially HER2, is evaluated in an enzyme-linked immunosorbent assay (ELISA) using a reagent, usually an antibody, to detect phosphorylated HER receptor, substrate, or downstream signaling molecule. Preferably, an antibody which detects phosphorylated HER2 is used. The assay may be performed on cell lysates, preferably from fresh or frozen biological samples.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxoids, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of Agrowth inhibitory@ antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g., from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g., a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells. Examples of HER2 antibodies that induce apoptosis are 7C2 and 7F3. See, in particular, WO98/17797.

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSARi®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem. Intl. Ed. Engl.*, 33:183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

Herein, a "taxoid" is a chemotherapeutic agent that functions to inhibit microtubule depolymerization. Examples include paclitaxel (TAXOL®), albumin-engineered nanoparticle formulation of paclitaxel (ABRAXANE™), and docetaxel (TAXOTERE®). The preferred taxoid is paclitaxel.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., Eur. J. Cancer, 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem., 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSAJ) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3 fluorophenyl) methoxy]phenyl]6[5[[[2-methylsulfonyl)ethyl]amino]methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVACJ) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

Herein, "standard of care" chemotherapy refers to the chemotherapeutic agents routinely used to treat a particular cancer. For example, for operable breast cancer, including node positive breast cancer, the standard of care adjuvant therapy can be anthracycline/cyclophosphamide (AC) chemotherapy, cyclophosphamide, methotrexate, fluorouracil (CMF) chemotherapy, fluorouracil, anthracycline and cyclophosphamide (FAC) chemotherapy, or AC followed by paclitaxel (T) (AC→T). For the patients described in the examples herein, "standard of care" has been AC→T treatment.

Where an anti-cancer agent, such as HERCEPTIN®, is administered as a "single agent" it is the only agent administered to the subject, during a treatment regimen, to treat the cancer, i.e., the agent is not provided in combination with other anti-cancer agents. However, such treatment includes the administration of other anti-cancer agents substantially prior to, or following, administration of the anti-cancer agent.

An Aanti-angiogenic agent@ refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mulerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

II. Production of Antibodies

A description follows as to exemplary techniques for the production of HER2 antibodies used in accordance with the present invention. The HER2 antigen to be used for production of antibodies may be, e.g., a soluble form of the extracellular domain of a HER2 receptor or a portion thereof, containing the desired epitope. Alternatively, cells expressing HER2 at their cell surface (e.g., NIH-3T3 cells transformed to overexpress HER2; or a carcinoma cell line such as SK-BR-3 cells, see Stancovski et al., *PNAS* (USA), 88:8691-8695 (1991)) can be used to generate antibodies. Other forms of HER2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Various methods for making monoclonal antibodies herein are available in the art. For example, the monoclonal antibodies may be made using the hybridoma method first described by Kohler et al., *Nature,* 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, Monoclonal *Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Pluckthun, *Immunol. Revs.,* 130: 151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352: 624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,*

21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al, *Nature,* 321:522-525 (1986); Riechmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.,* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

Humanization of murine 4D5 antibody to generate humanized variants thereof, including Trastuzumab, is described in U.S. Pat. Nos. 5,821,337, 6,054,297, 6,407,213, 6,639,055, 6,719,971, and 6,800,738, as well as Carter et al. *PNAS* (USA), 89:4285-4289 (1992). HuMAb4D5-8 (trastuzumab) bound HER2 antigen 3-fold more tightly than the mouse 4D5 antibody, and had secondary immune function (ADCC) which allowed for directed cytotoxic activity of the humanized antibody in the presence of human effector cells. HuMAb4D5-8 comprised variable light ($V_L$) CDR residues incorporated in a $V_L$ kappa subgroup I consensuse framework, and variable heavy ($V_H$) CDR residues incorporated into a $V_H$ subgroup III consensus framework. The antibody further comprised framework region (FR) substitutions as positions: 71, 73, 78, and 93 of the $V_H$ (Kabat numbering of FR residues; and a FR substitution at position 66 of the $V_L$ (Kabat numbering of FR residues). Trastuzumab comprises non-A allotype human gamma 1 Fc region.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807. Alternatively, phage display technology (McCafferty et al., *Nature,* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., *Current Opinion in Structural Biology,* 3:564-571 (1993). Several sources of V-gene segments can be used for phage display. Clackson et al., *Nature,* 352:624-628 (1991) isolated a diverse array of anti-oxazolone antibodies from a small random combinatorial library of V-genes derived from the spleens of immunized mice. A repertoire of V-genes from unimmunized human donors can be constructed and antibodies to a diverse array of antigens (including self-antigens) can be isolated essentially following the techniques described by Marks et al., *J. Mol. Biol.,* 222:581-597 (1991), or Griffith et al., *EMBO* 1, 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods,* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology,* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a Alinear Antibody®, e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T-cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (V$_H$) connected to a light-chain variable domain (V$_L$) by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.*, 147:60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells, *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |

TABLE 1-continued

| Original Residue | Exemplary Substitutions | Preferred Substitutions |
|---|---|---|
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining: (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry, second ed., pp.* 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Exemplary trastuzumab variants herein include those described in US2003/0228663A1 (Lowman et al.), including substitutions of one or more of the following $V_L$ positions: Q27, D28, N30, T31, A32, Y49, F53, Y55, R66, H91, Y92, and/or T94; and/or substitutions of one or more of $V_H$ positions: W95, D98, F100, Y100a, and/or Y102.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in U.S. Patent Application US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively, or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176:1191-1195 (1992) and Shopes, B. *J. Immunol.*, 148: 2918-2922 (1992). Homodimeric antibodies with enhanced anti-tumor activity may also be prepared using heterobifunctional cross-linkers as described in Wolff et al., *Cancer Research*, 53:2560-2565 (1993). Alternatively, an antibody can be engineered which has dual Fc regions and may thereby have enhanced complement lysis and ADCC capabilities. See Stevenson et al., *Anti-Cancer Drug Design*, 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. Nos. 6,194,551B1, 6,242,195B1, 6,528,624B1 and 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Screening for Antibodies with the Desired Properties

Techniques for generating antibodies have been described above. One may further select antibodies with certain biological characteristics, as desired.

To identify a HER2 antibody which binds to HER2 Domain IV bound by trastuzumab (HERCEPTIN®), one can evaluate the ability to bind to the isolated Domain IV peptide, Domain IV as present in HER2 ECD; or as it exists in the intact HER2 receptor (where the ECD or receptor can be isolated or present on the surface of a cell), etc. Optionally, one may evaluate whether the HER2 antibody of interest binds to the Trastuzumab or 4D5 epitope, or blocks or competes with binding of Trastuzumab or 4D5 to HER2; such antibodies would necessarily be considered to bind to HER2 Domain IV bound by trastuzumab (HERCEPTIN®). To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody blocks binding of an antibody, such as trastuzumab or 4D5 to HER2. See, also, Fendly et al., *Cancer Research*, 50:1550-1558 (1990), where cross-blocking studies were done on HER2 antibodies by direct fluorescence on intact HER2 positive cells. HER2 monoclonal antibodies were considered to share an epitope if each blocked binding of the other by 50% or greater in comparison to an irrelevant monoclonal antibody control. In the studies in Fendly et al. 3H4 and 4D5 bound to the same epitope. Alternatively, or additionally, epitope mapping can be performed by methods known in the art and/or one can study the antibody-HER2 structure (Franklin et al., *Cancer Cell*, 5:317-328 (2004)) to see what domain or epitope of HER2 is/are bound by the antibody.

Trastuzumab has been shown in both in vitro assays and in animals, to inhibit the proliferation of human tumor cells that overexpress HER2. Hudziak et al., *Mol. Cell. Biol.*, 9:1165-1172 (1989); U.S. Pat. No. 5,677,171; Lewis et al., *Cancer Immunol. Immunother*, 37:255-263 (1993); Pietras et al., *Oncogene*, 1998; 17:2235-49 (1998); and Baselga et al., *Cancer Res.*, 58:2825-2831 (1998). HERCEPTIN® has both cytostatic and cytotoxic effects on HER2-positive tumor cell lines (Lewis et al., (1993)).

In order to select another growth inhibitory HER2 antibody with this property, those in vitro or in vivo assays can be used to screen HER2 antibodies for growth inhibition biological activity. In particular, to identify growth inhibitory HER2 antibodies, one may screen for antibodies which inhibit the growth of cancer cells which overexpress HER2 in vitro. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the HER2 antibody is added per dish. After six days, the number of cells, compared to untreated cells are counted using an electronic COULTER® cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select HER2 antibodies that inhibit growth of HER2 positive tumors in vivo, xenograft studies, such as those in Pietras et al. (1998) and Baselga et al. (1998), can be used to screen HER2 antibodies for this property.

Trastuzumab is a mediator of antibody-dependent cellular cytotoxicity (ADCC). Hotaling et al., *Proc. Am. Assoc. Cancer Res.*, 37:471 (1996), Abstract 3215; Pegram et al., *Proc. Am. Assoc Cancer Res*, 38:602 (1997), Abstract 4044; U.S. Pat. Nos. 5,821,337, 6,054,297, 6,407,213, 6,639,055, 6,719, 971, and 6,800,738; Carter et al., *PNAS* (USA), 89:4285-4289 (1992); and Clynes et al., Nature Medicine, 6:443-6 (2000). Other HER2 antibodies which mediate ADCC can be identified using various assays, including those described in these references.

Trastuzumab has also been reported to inhibit HER2 ectodomain cleavage (Molina et al., *Cancer Res.*, 61:4744-4749 (2001)), and other HER2 antibodies with this function can be identified using the methodology used by Molina et al., for example.

HERCEPTIN® has also been reported to induce normalization and regression of tumor vasculature in HER2 positive human breast tumors by modulating the effects of angiogenic factors (Izumi et al., *Nature*, 416:279-80 (2002)). Other HER2 antibodies with this property can be identified using the experiments described in Izumi et al.

(ix) HERCEPTIN® Compositions

The HERCEPTIN® composition generally comprises a mixture of a main species antibody (comprising light and heavy chain sequences of SEQ ID NOS: 5 and 6, respectively), and variant forms thereof, in particular acidic variants (including deamidated variants). Preferably, the amount of such acidic variants in the composition is less than about 25%. See, U.S. Pat. No. 6,339,142. See, also, Harris et al., *J. Chromatography*, *B* 752:233-245 (2001) concerning forms of trastuzumab resolvable by cation-exchange chromatography, including Peak A (Asn30 deamidated to Asp in both light chains); Peak B (Asn55 deamidated to isoAsp in one heavy chain); Peak 1 (Asn30 deamidated to Asp in one light chain); Peak 2 (Asn30 deamidated to Asp in one light chain, and Asp102 isomerized to isoAsp in one heavy chain); Peak 3 (main peak form, or main species antibody); Peak 4 (Asp102 isomerized to isoAsp in one heavy chain); and Peak C (Asp102 succinimide (Asu) in one heavy chain). Such variant forms and compositions are included in the invention herein.

(x) Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos, *Anticancer Research*, 19:605-614 (1999); Niculescu-Duvaz and Springer *Adv. Drug Del. Rev.*, 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated. Maximal efficacy with minimal toxicity is sought thereby. Both polyclonal antibodies and monoclonal antibodies have been reported as useful in these strategies (Rowland et al., *Cancer Immunol. Immunother.*, 21:183-87 (1986)). Drugs used in these methods include daunomycin, doxorubicin, methotrexate, and vindesine. Toxins used in antibody-toxin conjugates include bacterial toxins such as diphtheria toxin, plant toxins such as ricin, small molecule toxins such as geldanamycin (Mandler et al., *Jour. of the Nat. Cancer Inst.*, 92(19):1573-1581 (2000); Mandler et al., *Bioorganic & Med. Chem. Letters*, 10:1025-1028 (2000); Mandler et al., *Bioconjugate Chem.*, 13:786-791 (2002)), maytansinoids (EP 1391213; Liu et al., *Proc. Natl. Acad. Sci. USA*, 93:8618-8623 (1996)), and calicheamicin (Lode et al., *Cancer Res.*, 58:2928 (1998); Hinman et al., *Cancer Res.*, 53:3336-3342 (1993)). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieties include: DM1; DM3; and DM4, having the structures:

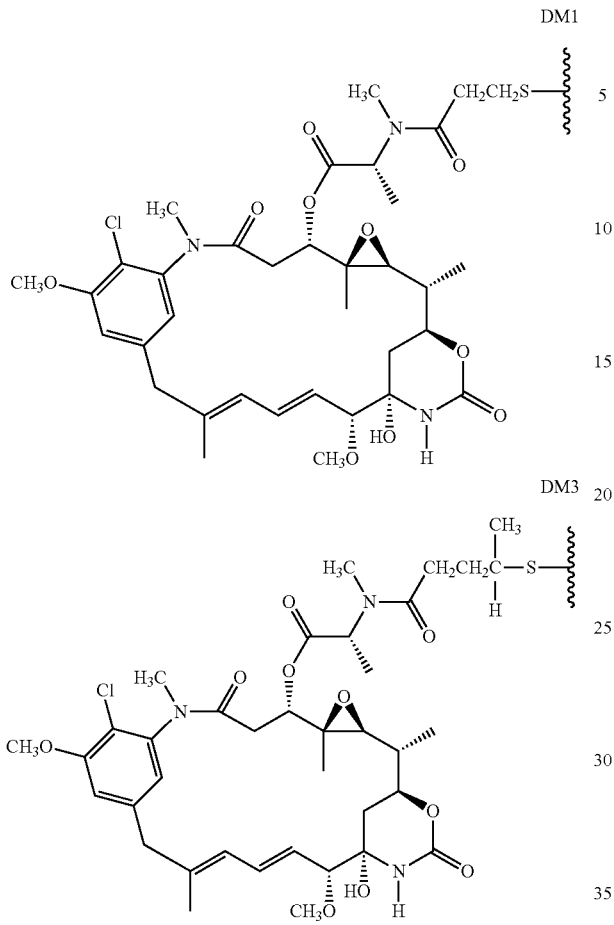
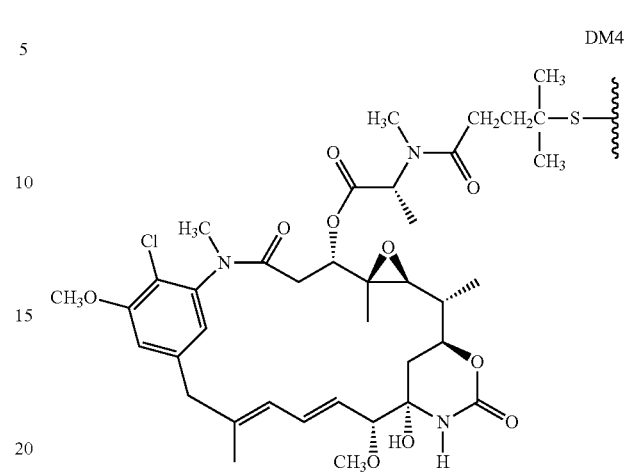
wherein, the wavy line indicates the covalent attachment of the sulfur atom of the drug to a linker (L) of an antibody drug conjugate. HERCEPTIN® (trastuzumab) linked by SMCC to DM1 has been reported (WO 2005/037992).
Other exemplary maytansinoid antibody drug conjugates have the following structures and abbreviations, (wherein Ab is antibody and p is 1 to about 8):
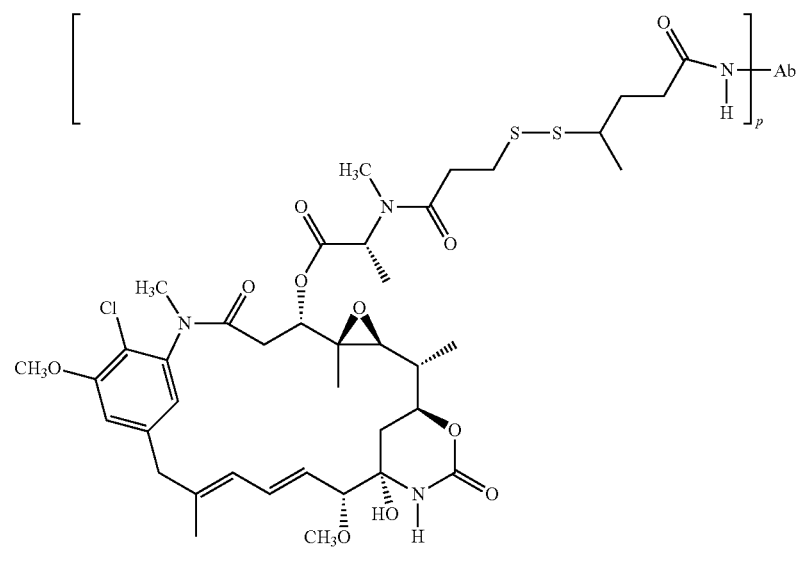
Ab-SPP-DM1

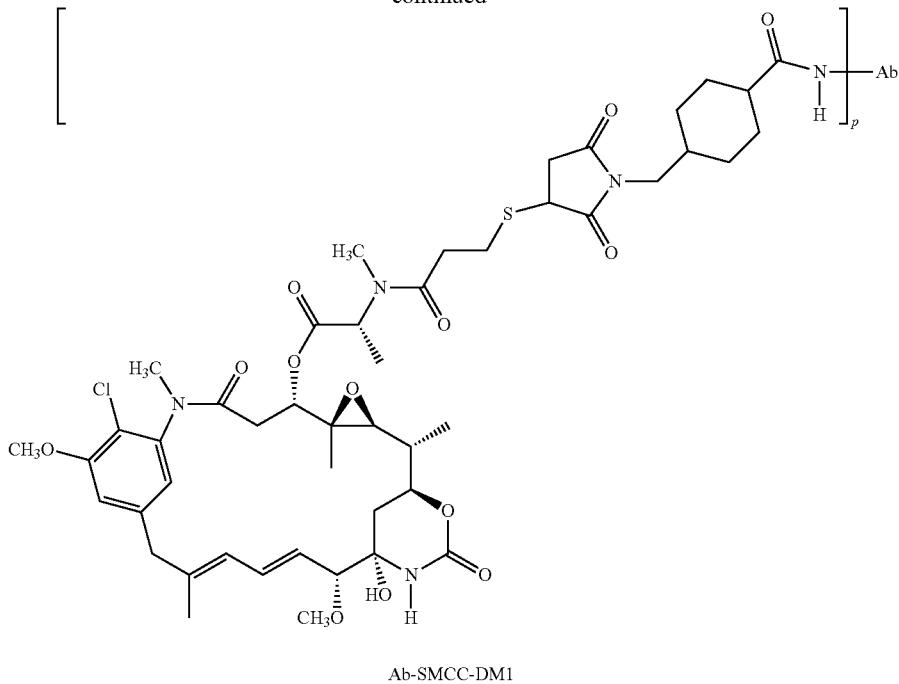

Ab-SMCC-DM1

Exemplary antibody drug conjugates where DM1 is linked through a BMPEO linker to a thiol group of the antibody have the structure and abbreviation:

human colorectal cancer. The conjugate was found to be highly cytotoxic towards cultured colon cancer cells, and showed antitumor activity in an in vivo tumor growth assay.

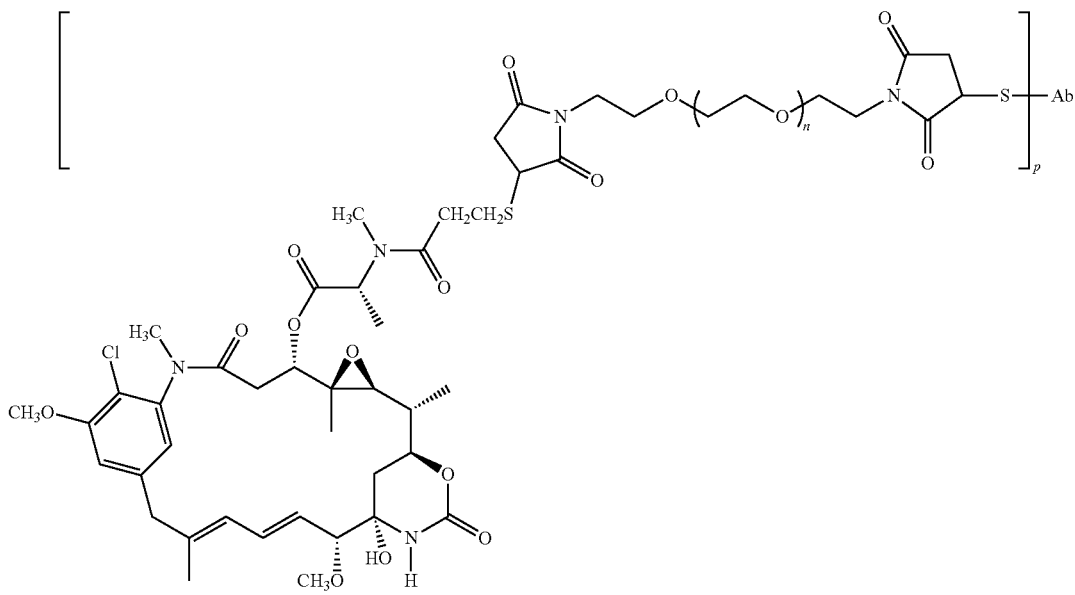

where Ab is antibody; n is 0, 1, or 2; and p is 1, 2, 3, or 4.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA*, 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., *Cancer Research*, 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds HER2. Antibody-maytansinoid conjugates are prepared by chemically linking an antibody to a maytansinoid molecule without significantly diminishing the biological activity of either the antibody or the maytansinoid molecule. See, e.g., U.S. Pat.

No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., *Cancer Research*, 52:127-131 (1992). Antibody-maytansinoid conjugates comprising the linker component SMCC may also be prepared. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly, preferred coupling agents include N-succinimidyl-3-(2-pyridyldithio) propionate (SPDP) (Carlsson et al., *Biochem. J.*, 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., *Antimicrob. Agents and Chemother.*, 45(12):3580-3584 (2001)) and have anticancer (U.S. Pat. No. 5,663,149) and antifungal activity (Pettit et al., *Antimicrob. Agents Chemother.*, 42:2961-2965 (1998)). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al., *Proceedings of the American Association for Cancer Research*, Volume 45, Abstract Number 623, presented Mar. 28, 2004.

An exemplary auristatin embodiment is MMAE (wherein the wavy line indicates the covalent attachment to a linker (L) of an antibody drug conjugate).

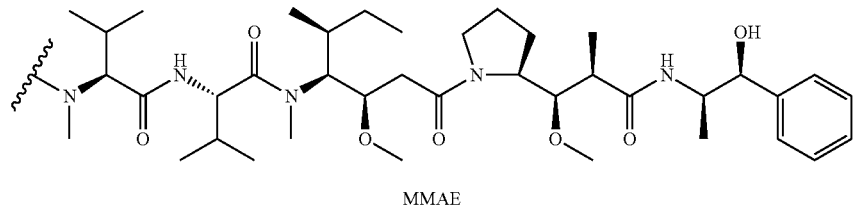 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF (wherein the wavy line indicates the covalent attachment to a linker (L) of an antibody drug conjugate):

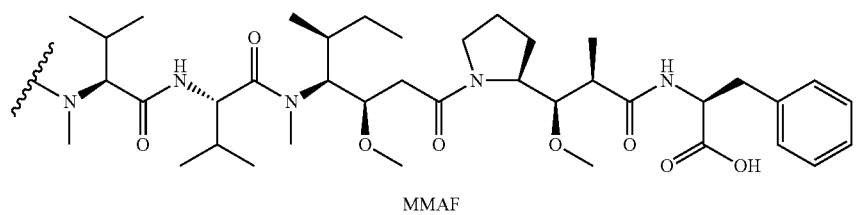

MMAF

Additional exemplary embodiments comprising MMAE or MMAF and various linker components (described further herein) have the following structures and abbreviations (wherein Ab means antibody and p is 1 to about 8):

$\gamma_1^1$, PSAG and $\theta^1_1$ (Hinman et al., *Cancer Research,* 53:3336-3342 (1993), Lode et al., *Cancer Research,* 58:2925-2928 (1998) and the aforementioned U.S. patents to American Cyanamid). Another anti-tumor drug that the antibody can be

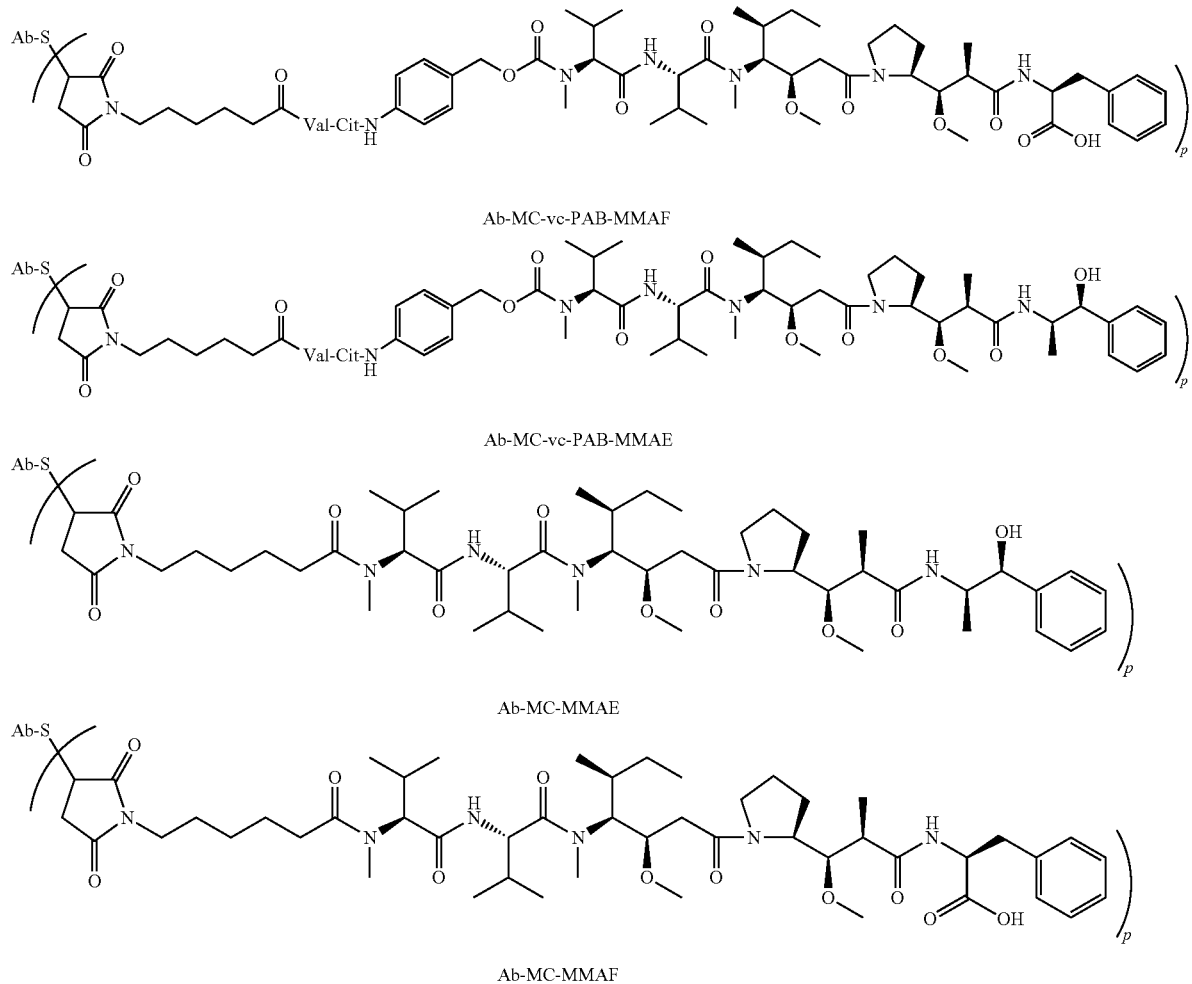

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, Academic Press (1965)) that is well known in the field of peptide chemistry. The auristatin/dolastatin drug moieties may be prepared according to the methods of: U.S. Pat. Nos. 5,635,483; 5,780,588; Pettit et al., *J. Am. Chem. Soc.,* 111:5463-5465 (1989); and Pettit et al., *Anti-Cancer Drug Design,* 13:243-277 (1998).

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712, 374, 5,714,586, 5,739,116, 5,767,285, 5,770,701, 5,770,710, 5,773,001, 5,877,296 (all assigned to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al., *Cancer Research,* 53:3336-3342 (1993), Lode et al., *Cancer Research,* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The method disclosed in Fraker et al., *Biochem. Biophys. Res. Commun.*, 80:49-57 (1978) can be used to incorporate iodine-123.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research*, 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

In the antibody drug conjugates (ADC) of the invention, an antibody (Ab) is conjugated to one or more drug moieties (D), e.g., about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad\qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Exemplary linker component structures are shown below (wherein the wavy line indicates sites of covalent attachment to other components of the ADC):

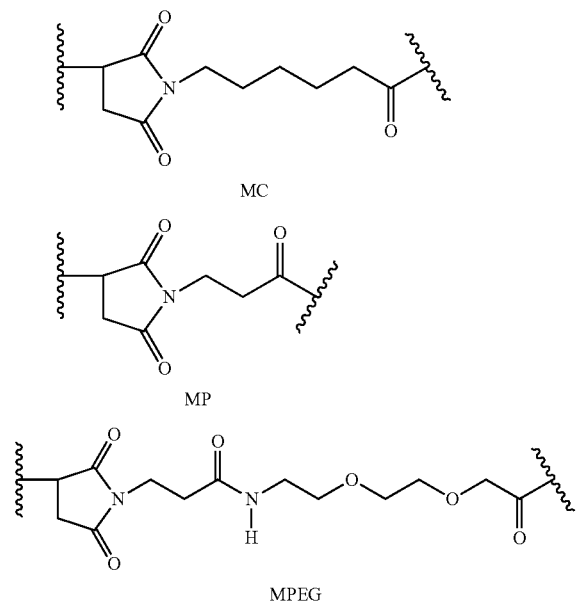

MC

MP

MPEG

Additional exemplary linker components and abbreviations include (wherein the antibody (Ab) and linker are depicted, and p is 1 to about 8):

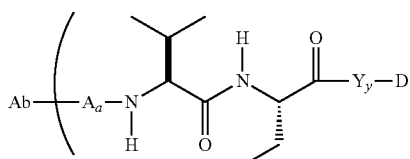
Val-cit

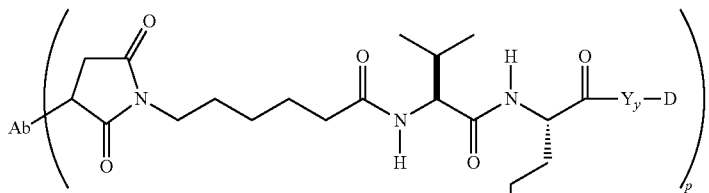
MC-val-cit

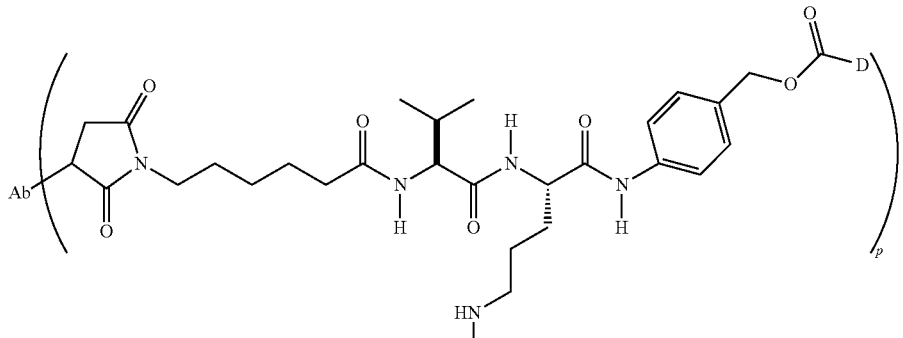
MC-val-cit-PAB

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh,

*Bioconjugate Chem.* 3:138-146 (1992); U.S. Pat. No. 5,362, 852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Other immunoconjugates are contemplated herein. For example, the antibody or antibody fragment may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide interchange reaction. A chemotherapeutic agent is optionally contained within the liposome. See Gabizon et al., *J. National Cancer Inst.*, 81(19) 1484 (1989).

III. Selecting Patients for Therapy

The patient herein is generally subjected to a diagnostic test prior to therapy so as to identify HER2 positive subjects. For example, the diagnostic test may evaluate HER2 expression (including overexpression), amplification, and/or activation (including phosphorylation or dimerization).

Generally, if a diagnostic test is performed, a sample may be obtained from a patient in need of therapy. Where the subject has cancer, the sample is generally a tumor sample. In the preferred embodiment, the tumor sample is from a breast cancer biopsy. The biological sample herein may be a fixed sample, e.g., a formalin fixed, paraffin-embedded (FFPE) sample, or a frozen sample.

To determine HER2 expression or amplification in the cancer, various diagnostic/prognostic assays are available. In one embodiment, HER2 overexpression may be analyzed by IHC, e.g., using the HERCEPTEST® (Dako). Parrafin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0–10,000 copies/cell,
1+= at least about 200,000 copies/cell,
2+= at least about 500,000 copies/cell,
3+= at least about 2,000,000 copies/cell.

Overexpression of HER2 at the 3+ level, which leads to ligand-independent activation of the tyrosine kinase (Hudziak et al., *Proc. Natl. Acad. Sci. USA*, 84:7159-7163 (1987)), occurs in approximately 30% of breast cancers, and in these patients, relapse-free survival and overall survival are diminished (Slamon et al., *Science*, 244:707-712 (1989); Slamon et al., *Science*, 235:177-182 (1987)).

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of HER2 amplification in the tumor.

HER2 positivity may also be evaluated using an in vivo diagnostic assay, e.g. by administering a molecule (such as an antibody) which binds the molecule to be detected and is tagged with a detectable label (e.g., a radioactive isotope) and externally scanning the patient for localization of the label.

Other methods for identifying HER2 positive tumors are contemplated herein, including but not limited to measuring shed antigen, and detecting HER2 positive tumors indirectly, such as by evaluating downstream signaling mediated through HER2 receptor, gene expression profiling, etc.

Preferably, subjects are selected which have a HER2 positive tumor or sample which overexpresses HER2 as evaluated by immunohistochemistry (IHC) and/or has amplified HER2 gene as evaluated by FISH.

IV. Pharmaceutical Formulations

Therapeutic formulations of the HER2 antibodies used in accordance with the present invention are prepared for storage by mixing an antibody having the desired degree of purity with optional pharmaceutically acceptable carriers, excipients or stabilizers (Remington's *Pharmaceutical Sciences* 16th edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENJ, PLURONICSJ or polyethylene glycol (PEG).

Lyophilized antibody formulations are described in U.S. Pat. Nos. 6,267,958, 6,685,940 and 6,821,515, expressly incorporated herein by reference. The preferred HERCEPTIN® formulation is a sterile, white to pale yellow preservative-free lyophilized powder for intravenous (IV) administration, comprising 440 mg trastuzumab, 400 mg α, α-trehalose dihydrate, 9.9 mg L-histidine-HCl, 6.4 mg L-histidine, and 1.8 mg polysorbate 20, USP. Reconstitution of 20 mL of bacteriostatic water for injection (BWFI), containing 1.1% benzyl alcohol as a preservative, yields a multi-dose solution containing 21 mg/mL trastuzumab, at pH of approximately 6.0.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

The formulation herein may also contain more than one active compound as necessary for the particular indication being treated, preferably those with complementary activities that do not adversely affect each other. Various drugs which can be combined with the HER2 antibody are described in the Adjuvant Therapy section below. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

V. Adjuvant Therapy

The present invention provides a method of adjuvant therapy comprising administering to a human subject with nonmetastatic HER2 positive breast cancer, following definitive surgery, an antibody which binds to HER2 Domain IV bound by trastuzumab (HERCEPTIN®), in an amount effective to extend disease free survival (DFS) or overall survival (OS), wherein the DFS or the OS is evaluated about 2 to 5 years after an initial administration of the antibody. Preferably the subject's DFS or OS is evaluated about 3-5 years, about 4-5 years, or at least about 4, or at least about 5 years after initiation of treatment or after initial diagnosis. Preferably, the antibody is trastuzumab (HERCEPTIN®).

The subject treated herein is generally at high risk of recurrence. Where the subject's tumor is HER2 positive, this is known to be more aggressive, and linked to a higher likelihood of recurrence. In addition, the subject may be at increased risk due to younger age (for instance, where the subject is less than about 50 years old); may have had a large primary tumor (for example a tumor greater than 2 centimeters in diameter); may be lymph node-positive (for example, having 4 or more involved lymph nodes, including 4-9 involved lymph nodes, and 10 or more involved lymph nodes); may be estrogen receptor (ER) negative; and/or may be progesterone receptor (PG) negative.

The HER2 antibody is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Preferred dosages for the HER2 antibody are in the range from about 1 mg/kg to about 20 mg/kg, most preferably from about 2 mg/kg to about 12 mg/kg. Preferred dosage regimens for trastuzumab include 4 mg/kg trastuzumab administered as a 90-minute infusion, followed by a weekly maintenance dose of 2 mg/kg trastuzumab which can be administered as a 30-minute infusion if the initial loading dose is well tolerated. Other dosage regimens for trastuzumab are however contemplated, including less than weekly dosing, for example administration every 3 weeks, for example at a dose of 6 mg/kg, 8 mg/kg or 12 mg/kg; and including an initial dose of 8 mg/kg, followed by 6 mg/kg every three weeks (see, U.S. Pat. No. 6,627,196 B1, Baughman et al.; Leyland-Jones et al., *J. Clin. Oncol.*, 21:3965-71 (2003)). The number of doses of Trastuzumab administered may be at least 20 or more, preferably at least 50, for example 52 doses (where the antibody is administered every week). Where less frequent dosing of Trastuzumab is used, such as every 3 week dosing, fewer doses may be administered. Generally, the subject will receive Trastuzumab for at least about 1 year, and the subject's progress will be followed after that time.

While the HER2 antibody may be administered as single agent, the patient is preferably treated with a combination of the HER2 antibody, and one or more chemotherapeutic agent(s). Preferably at least one of the chemotherapeutic agents is a taxoid. The combined administration includes coadministration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the HER2 antibody. In this embodiment, the timing between at least one administration of the chemotherapeutic agent and at least one administration of the HER2 antibody is preferably approximately 1 month or less, and most preferably approximately 2 weeks or less. Alternatively, the chemotherapeutic agent and the HER2 antibody are administered concurrently to the patient, in a single formulation or separate formulations. Treatment with the combination of the chemotherapeutic agent (e.g., taxoid) and the HER2 antibody (e.g., trastuzumab) may result in a synergistic, or greater than additive, therapeutic benefit to the patient.

The chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner. Where the chemotherapeutic agent is paclitaxel, preferably, it is administered every week (e.g., at 80 mg/m$^2$) or every 3 weeks (for example at 175 mg/m$^2$ or 135 mg/m$^2$). Suitable docetaxel dosages include 60 mg/m$^2$, 70 mg/m$^2$, 75 mg/m$^2$, 100 mg/m$^2$ (every 3 weeks); or 35 mg/m$^2$ or 40 mg/m$^2$ (every week).

Various chemotherapeutic agents that can be combined are disclosed above. Preferred chemotherapeutic agents to be combined with the HER2 antibody are selected from the group consisting of a taxoid (including docetaxel and paclitaxel), vinca (such as vinorelbine or vinblastine), platinum compound (such as carboplatin or cisplatin), aromatase inhibitor (such as letrozole, anastrazole, or exemestane), antiestrogen (e.g., fulvestrant or tamoxifen), etoposide, thiotepa, cyclophosphamide, methotrexate, liposomal doxorubicin, pegylated liposomal doxorubicin, capecitabine, gemcitabine, COX-2 inhibitor (for instance, celecoxib), or proteosome inhibitor (e.g., PS342).

Most preferably, the HER2 antibody is combined with a taxoid, such as paclitaxel or docetaxel, optionally in combination with at least one other chemotherapeutic agent, such as a platinum compound (for example carboplatin or cisplatin).

Where an anthracycline (e.g., doxorubicin or epirubicin) is administered to the subject, preferably this is given prior to and/or following administration of the HER2 antibody, such as in the protocols disclosed in Example 1 below where an anthracycline/cyclophosphomide combination was administered to the subject following surgery, but prior to administration of the HER2 antibody and taxoid. However, a modified anthracycline, such as liposomal doxorubicin (TLC D-99; (MYOCET®), pegylated liposomal doxorubicin (CAELYX®), or epirubicin, with reduced cardiac toxicity, may be combined with the HER2 antibody.

Administration of the antibody and chemotherapy can decrease disease recurrence (cancer recurrence in the breast and/or distant recurrence), in a population of subjects by about 50% at 3 years (where "about 50%" herein, includes a range from about 45% to about 70%), for example decreases recurrence in the breast by about 52% at 3 years, and/or decreases distant recurrence by about 53% at 3 years, compared to subjects treated with chemotherapy (e.g., taxoid, such as paclitaxel) alone.

The invention herein provides a method of curing nonmetastatic breast cancer in a population of human subjects with nonmetastatic HER2 positive breast cancer comprising administering an effective amount of trastuzumab (HERCEPTIN®) and a taxoid to the subjects following definitive surgery, and evaluating the subjects after four (or more) years to confirm no disease recurrence has occurred in at least about 80% (preferably at least about 85%) of the subjects. The population may comprise 3000 or more human subjects.

The invention further concerns a method of decreasing disease recurrence in a population of human subjects with nonmetastatic HER2 positive breast cancer comprising administering an effective amount of trastuzumab (HERCEPTIN®) and a taxoid to the subjects following definitive surgery, wherein disease recurrence is decreased by at least about 50% at 3 years compared to subjects treated with taxoid alone.

Aside from the HER2 antibody and the chemotherapeutic agent, other therapeutic regimens may be combined therewith. For example, a second (third, fourth, etc) chemotherapeutic agent(s) may be administered, wherein the second chemotherapeutic agent is either another, different taxoid chemotherapeutic agent, or a chemotherapeutic agent that is not a taxoid. For example, the second chemotherapeutic agent may be a taxoid (such as paclitaxel or docetaxel), a vinca (such as vinorelbine), a platinum compound (such as cisplatin or carboplatin), an anti-hormonal agent (such as an aromatase inhibitor or antiestrogen), gemcitabine, capecitabine, etc. Exemplary combinations include taxoid/platinum compound, gemcitabine/taxoid, gemcitabine/vinorelbine, vinorelbine/taxoid, capecitabine/taxoid, etc. "Cocktails" of different chemotherapeutic agents may be administered. Exemplary chemotherapy cocktails include: TAC (TAXOTERE®, ADRIAMYCIN®, cyclophosphamide); CEF (cyclophosphamide administered orally, epirubicin, 5-FU); CMF (cyclophosphamide, methotrexate, 5-FU); dose dense ACT (ADRIAMYCIN® administered every 2 weeks with cytokine support, G-CSF, cyclophosphamide, TAXOTERE®), AC (ADRIAMYCIN®, cyclophosphamide); FEC (5-FU, epirubicin, cyclophosphamide, all drugs administered intravenously); FAC (5-FU, ADRIAMYCIN®, cyclophosphamide).

The preferred treatment regimen herein comprises lumpectomy/mastectomy and axilliary dissection with pathologically involved lymph nodes, followed by anthracycline+cyclosphosphomide (AC), for example for 4 cycles, then administration of a taxoid with HERCEPTIN® for about one year.

Other therapeutic agents that may be combined with the HER2 antibody include any one or more of: a second, different HER2 antibody (for example, a HER2 heterodimerization inhibitor such as pertuzumab, or a HER2 antibody which induces apoptosis of a HER2-overexpressing cell, such as 7C2, 7F3 or humanized variants thereof); an antibody directed against a different tumor associated antigen, such as EGFR, HER3, HER4; anti-hormonal compound or endocrine therapeutic, e.g., an anti-estrogen compound such as tamoxifen, or an aromatase inhibitor; a cardioprotectant (to prevent or reduce any myocardial dysfunction associated with the therapy); a cytokine; an EGFR inhibitor (such as TARCEVA®, IRESSA® or cetuximab); an anti-angiogenic agent (especially bevacizumab sold by Genentech under the trademark AVASTIN®); a tyrosine kinase inhibitor; a COX inhibitor (for instance a COX-1 or COX-2 inhibitor); nonsteroidal anti-inflammatory drug, celecoxib (CELEBREX®); farnesyl transferase inhibitor (for example, Tipifarnib/ZARNESTRA™ R115777 available from Johnson and Johnson or Lonafarnib SCH66336 available from Schering-Plough); HER2 vaccine (such as HER2 AutoVac vaccine from Pharmexia, or APC8024 protein vaccine from Dendreon, or HER2 peptide vaccine from GSK/Corixa); another HER targeting therapy (e.g. trastuzumab, cetuximab, ABX-EGF, EMD7200, gefitinib, erlotinib, CP724714, CI1033, GW572016, IMC-11F8, TAK165, etc.); Raf and/or ras inhibitor (see, for example, WO 2003/86467); doxorubicin HCl liposome injection (DOXIL®); topoisomerase I inhibitor such as topotecan; taxoid; HER2 and EGFR dual tyrosine kinase inhibitor such as lapatinib/GW572016; TLK286 (TELCYTA®); EMD-7200; AB1007 (Factor XII heavy chain antibody, B7C9); everolimis (CERTICAN®); sirolimus (rapamycin, RAPAMUNE®); a body temperature-reducing medicament such as acetaminophen, diphenhydramine, or meperidine; hematopoietic growth factor, etc.

Suitable dosages for any of the above coadministered agents are those presently used and may be lowered due to the combined action (synergy) of the agent and HER2 antibody.

In addition to the above therapeutic regimes, the patient may be subjected to radiation therapy.

Preferably the administered HER2 antibody is an intact, naked antibody. However, the HER2 antibody may be conjugated with a cytotoxic agent. Preferably, the conjugated antibody and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

VI. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

EXAMPLE 1

This example concerns a joint interim analysis of results obtained in human breast cancer subjects treated in National Surgical Adjuvant Breast and Bowel Project (NSABP B-31) and the North Central Cancer Treatment Group (NCCTG) Intergroup N9831 breast cancer clinical trials. The NCCTG study enrolled its first patient in June 2000 and has enrolled 3,406 patients to date; the NSABP study began enrollment in March 2000 and has enrolled 2,085 patients to date. The interim analysis of this example was based on information from 3,300 patients. These trials evaluated the efficacy of trastuzumab (HERCEPTIN®) as adjuvant therapy for high risk operable breast cancer.

Study Design

The design of the NSABP B-31 and NCCTG N9831 studies is depicted in FIG. 4A.

In the NSABP B-31 trial, subjects were treated with anthracycline (60 mg/m$^2$) plus cyclophosphamide (600 mg/m$^2$), every 3 weeks, for four cycles (q 3 wk×4) then received either: paclitaxel (TAXOL®) (175 mg/m$^2$), every 3 weeks, for 4 cycles (q 3 wk×4) (Arm 1), or paclitaxel (175 mg/m$^2$) every 3 weeks, for 4 cycles and trastuzumab (4 mg/kg/wk loading dose (LD) for 4 weeks), followed by 2 mg/kg/wk maintenance dose for 51 weeks (Arm 2).

In the NCCTG N9831 trial, which is an amended version of the NSABP B-31 trial, the following treatment protocol was used:

Arm A: anthracycline (60 mg/m$^2$) plus cyclophosphamide (600 mg/m$^2$), every 3 weeks, for four cycles (q 3 wk×4) followed by paclitaxel (80 mg/m$^2$/wk) for 12 weeks.

Arm B: anthracycline (60 mg/m$^2$) plus cyclophosphamide (600 mg/m$^2$), every 3 weeks, for four cycles (q 3 wk×4), followed by paclitaxel (80 mg/m$^2$/wk) for 12 weeks, followed by trastuzumab (4 mg/kg/wk loading dose (LD) for 4 weeks and 2 mg/kg/wk maintenance dose for 51 weeks).

Arm C: anthracycline (60 mg/m$^2$) plus cyclophosphamide (600 mg/m$^2$), every 3 weeks, for four cycles (q 3 wk×4), followed by paclitaxel (80 mg/m$^2$/wk) for 12 weeks and trastuzumab (4 mg/kg/wk loading dose (LD) for 4 weeks and 2 mg/kg/wk maintenance dose for 51 weeks).

Figure 4B:
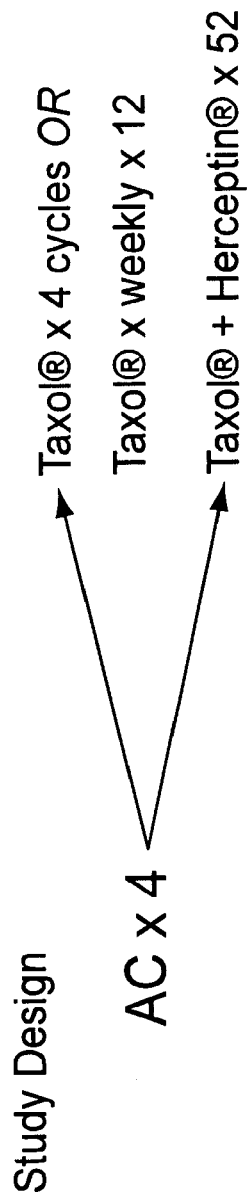
FIG. 4B depicts the study design used for the joint analysis of the NSABP B31 and NCCTG N9831 (Intergroup) study results. AC=anthracycline/cyclophosphomide combination. Efficacy data in Example 1 herein included from all subjects from NSABP B-31 but excludes the patients from Intergroup who did not start HERCEPTIN® simultaneously with TAXOL® (arm 2).

The arms used in the joint analysis of the two study designs are depicted in FIG. 4B.

HERCEPTIN® is a sterile, white to pale yellow preservative-free lyophilized powder for intravenous (IV) administration. The nominal content of each HERCEPTIN® vial is 440 mg trastuzumab, 400 mg α, α-trehalose dihydrate, 9.9 mg L-histidine-HCl, 6.4 mg L-histidine, and 1.8 mg polysorbate 20, USP. Reconsitution of 20 mL of the supplied bacteriostatic water for injection (BWFI), containing 1.1% benzyl alcohol as a preservative, yields a multi-dose solution containing 21 mg/mL trastuzumab, at pH of approximately 6.0. HERCEPTIN® was administered as a loading dose of 4 mg/kg, following by maintenance dose of 2 mg/kg every week.

To qualify for these trials, patients were required to have invasive breast cancer, resected by either lumpectomy, or total mastectomy, plus axillary dissection, with pathologically involved axillary nodes. The protocol, as amended in N9831 allowed the enlistment of high risk node negative patients. Patients were not allowed to have locally advanced or distant disease, had normal hematologic, hepatic, and renal function, received no prior anthracycline or taxanes therapy, and had no significant sensory/motor neuropathy. The patients were HER2 positive by FISH or +++ by immunohistochemistry (IHC) verified centrally (N9831) or by approved reference lab (B-31).

The patient and tumor characteristics for the subjects in these studies are shown in FIG. 5. The joint analysis population represents a very high risk group for recurrence and death compared to more typical subjects included in adjuvant clinical trials. In particular, the subjects: are younger (median age=48); have larger tumors (60% greater than 2 cm); have more involved lymph nodes (14-15% had more than 10 involved lymph nodes); and all were HER2 positive (HER2+). Outcomes of the treated population were expected to be very poor with currently available chemotherapy.

Results

The primary endpoint of these trials was disease free survival (DFS), analyzed according to the intent-to-treat principle, ie, patients were evaluated on the basis of their assigned therapy. Secondary endpoints were overall survival (OS) and Time to 1st Distant Recurrence. Definite analysis was scheduled after 710 DFS events. The first interim analysis was scheduled after 355 DFS events, then every 6 months thereafter; a total of 395 events on both trials are reported herein. The trials were to be stopped only if equivalence was rejected at p=0.0005 (2p=0.001).

Figure 6:
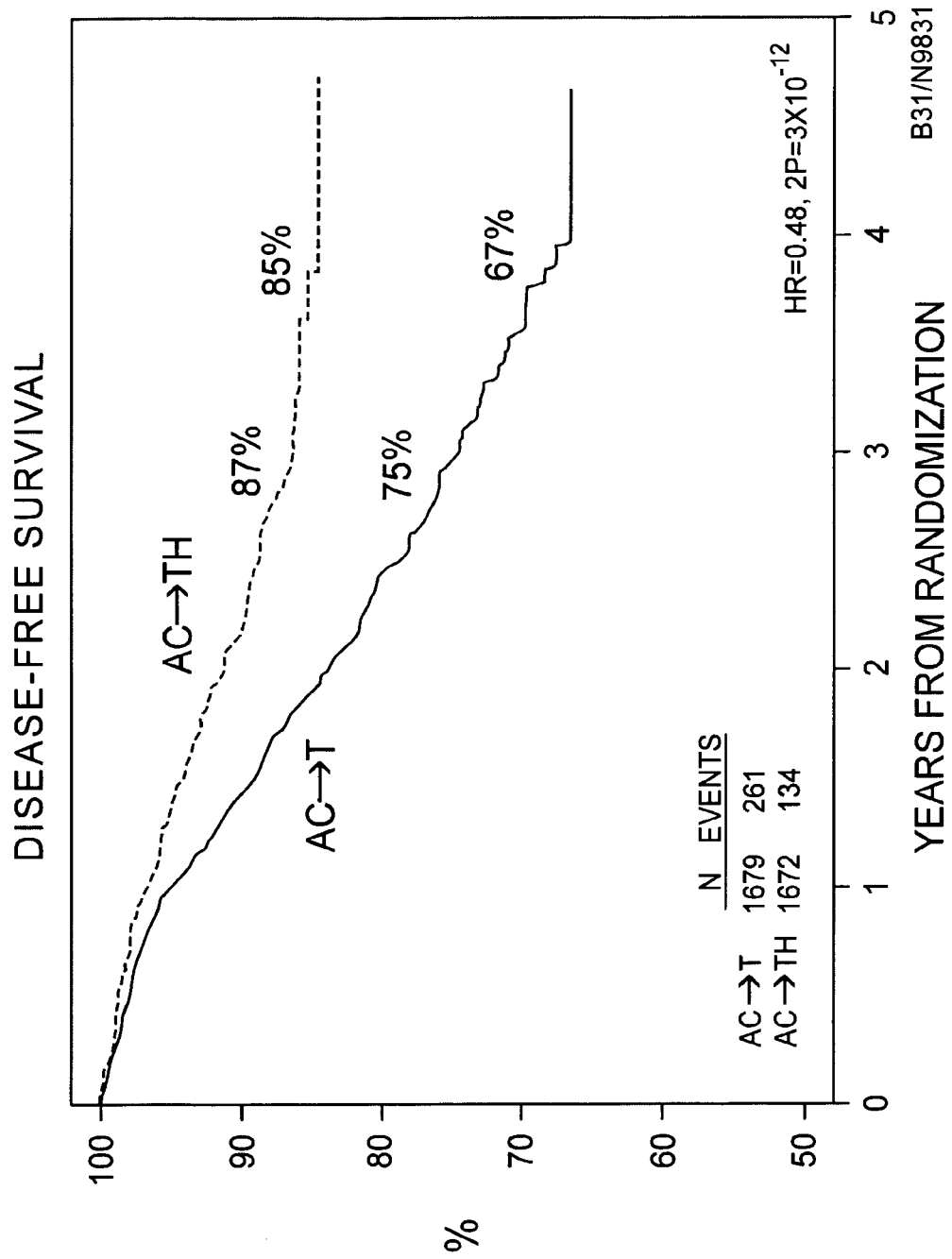
FIG. 6 represents disease-free survival for the B31/N9831 studies

The DFS for the combined B31 and N9831 study results is shown in FIG. 6.

Figure 7:
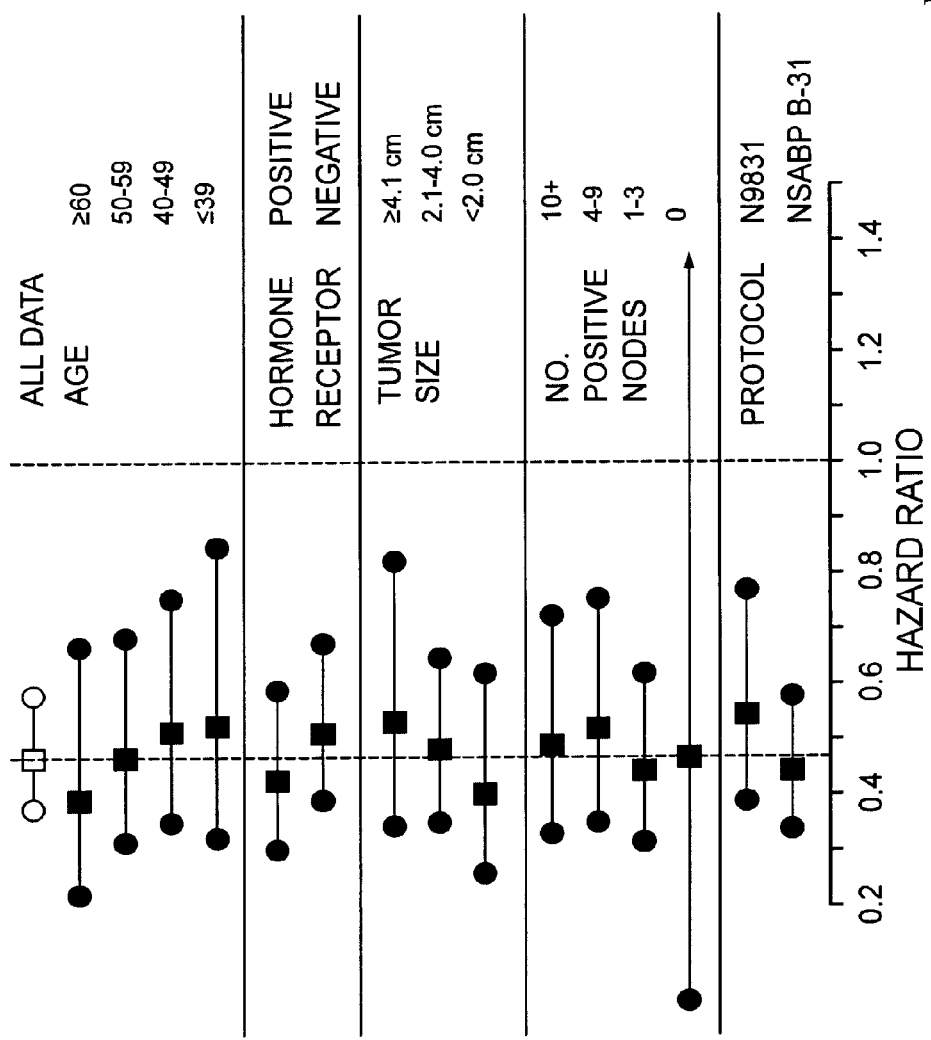
FIG. 7 is a Forest plot for disease-free survival, where patients are grouped by age, hormone status, tumor size, and number of positive nodes.

FIG. 7 presents the DFS data for various patient groups, classified based upon age, hormone receptor status, tumor size, and number of positive nodes, relative to all data (from both studies), and expressed as a hazard ratio. The individual results for the two studies (N9831 and B-31, respectively) are shown at the bottom of the plot.

Figure 8:
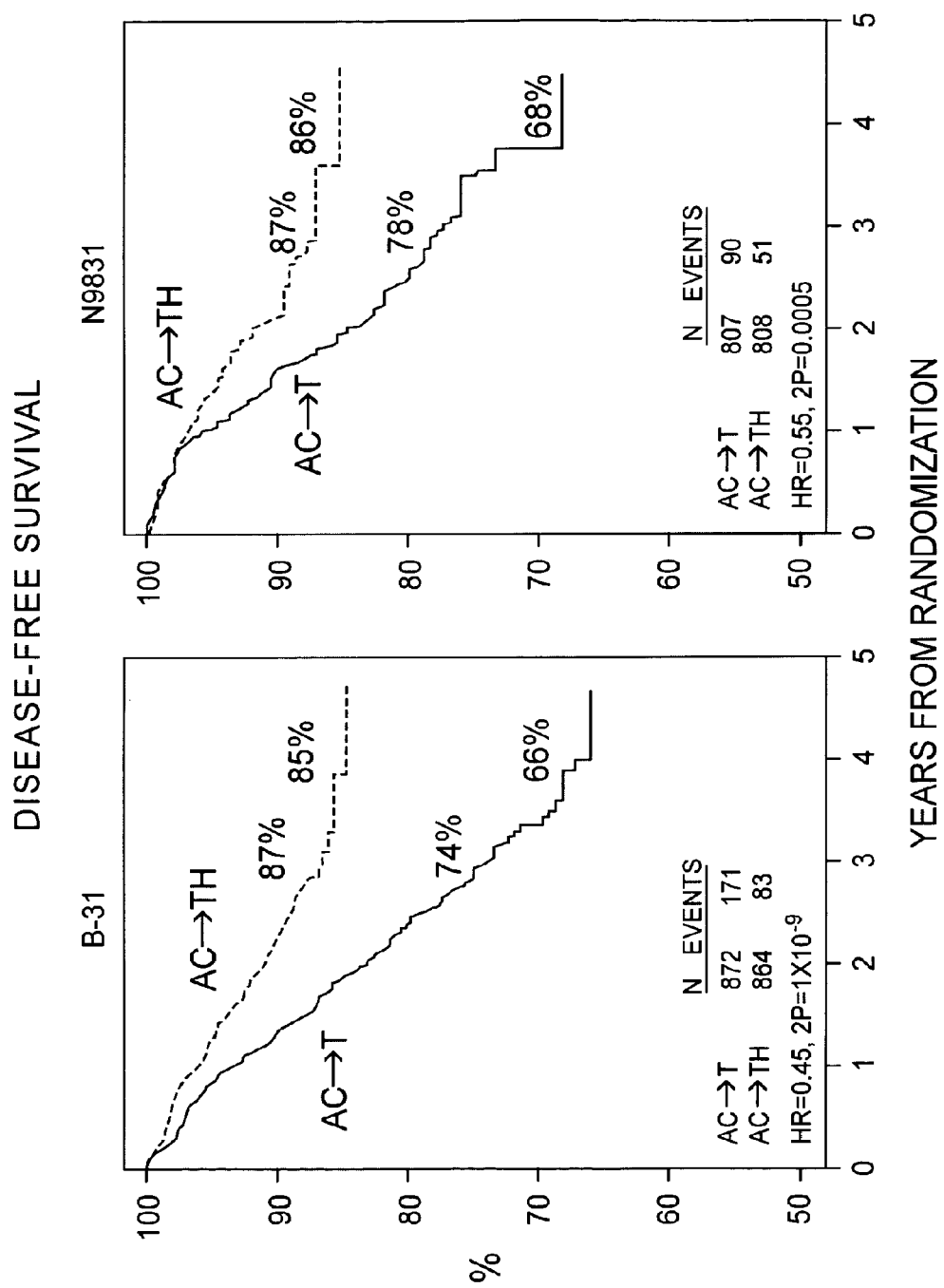
FIG. 8 shows disease-free survival for the AC→T and AC→TH arms of the B-31 (left panel) and N9831 (right panel) studies.

FIG. 8 shows the DFS results for the N9831 and B-31 trials individually.

Figure 9:
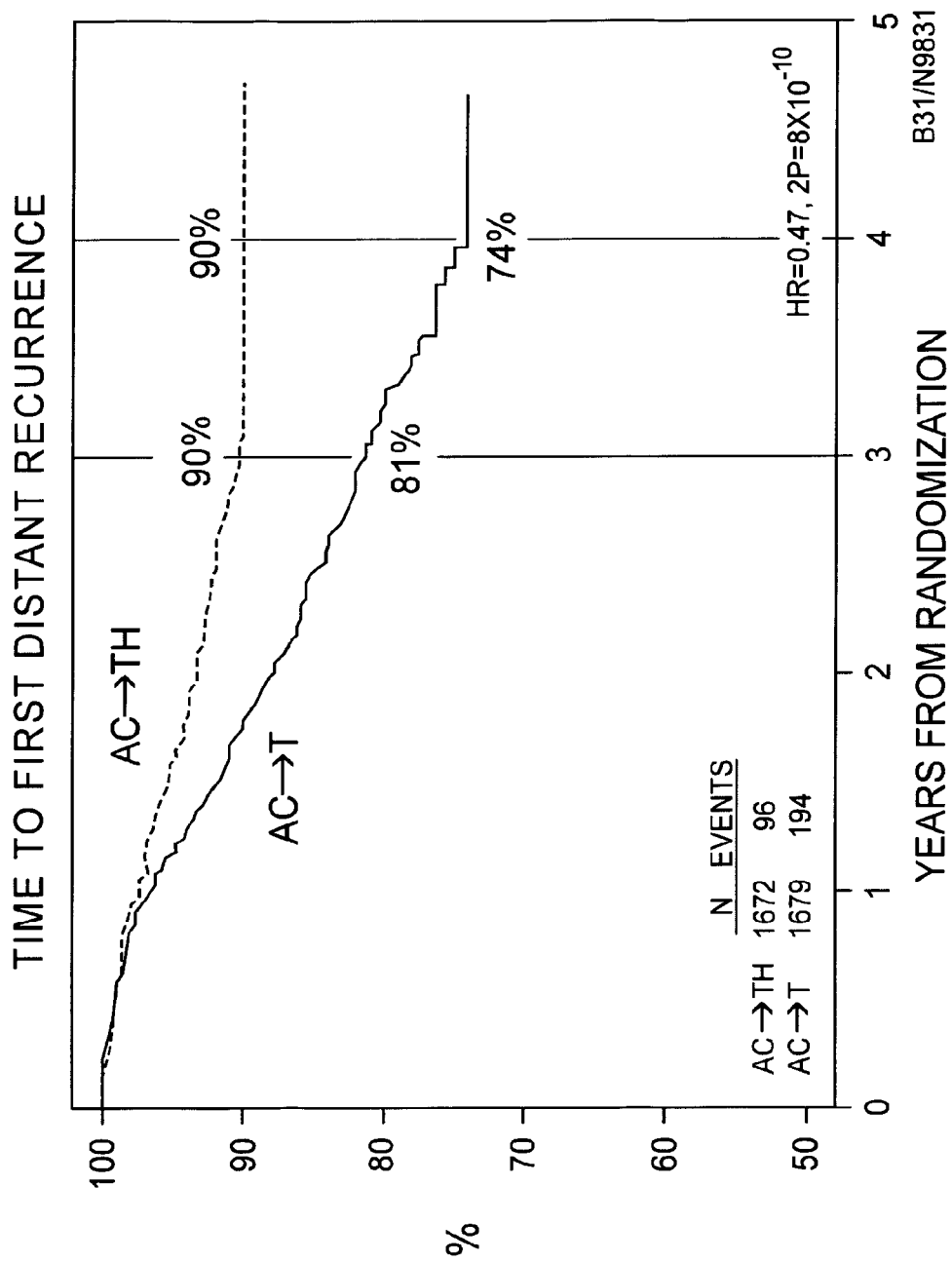
FIG. 9 shows time to distant recurrence for the AC→T and AC→TH arms of the B31/N9831 studies.

Time to First Distant Recurrence for the combined results of N9831 and B-31 is shown in FIG. 9.

Figure 10:
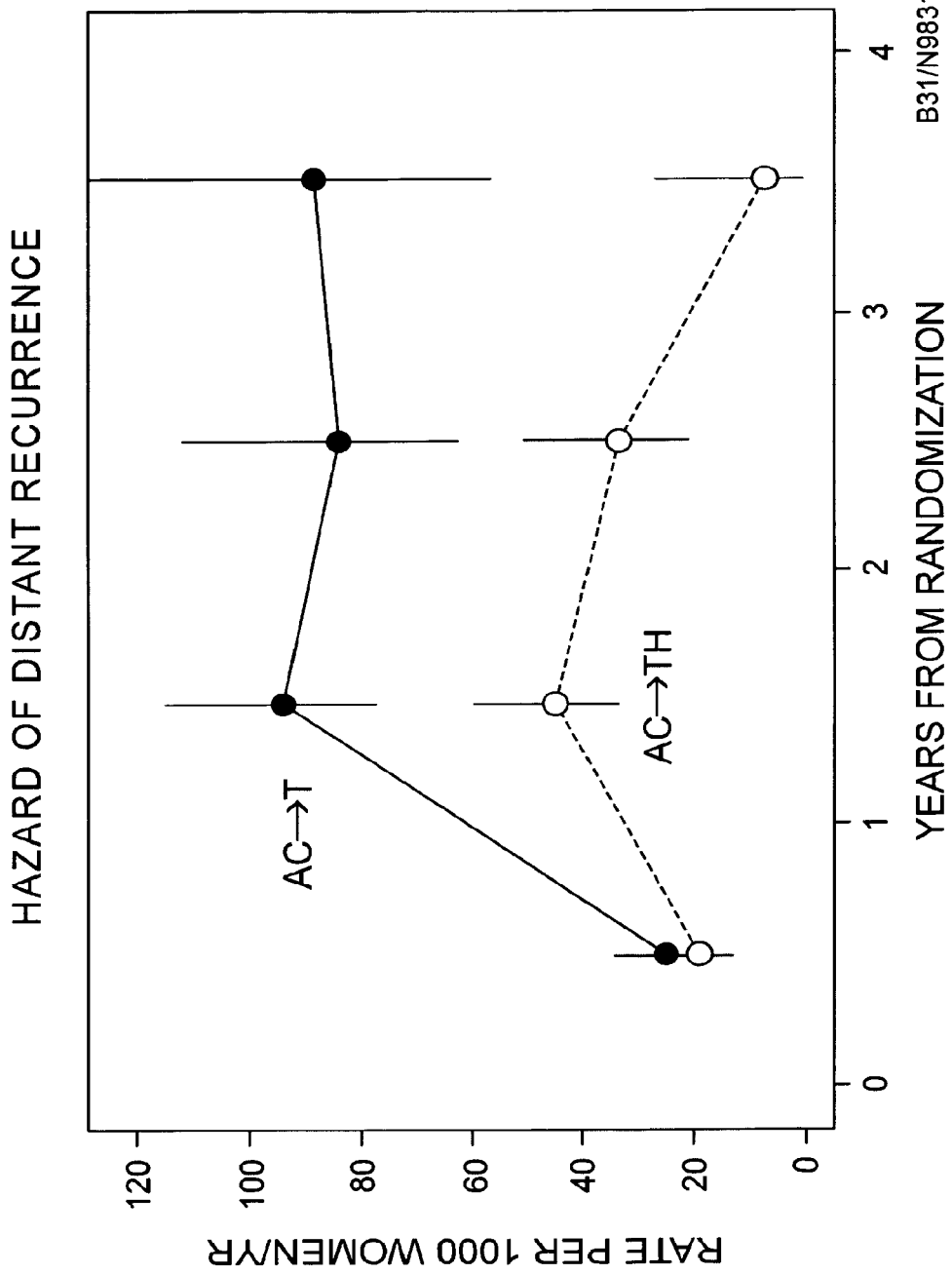
FIG. 10 depicts hazard of distant recurrence for the AC→T and AC→TH arms of the B31/N9831 studies.

FIG. 10 depicts the Hazard of Distant Recurrence for randomized trials B31/N9831, for patients treated with anthracycline and cyclophosphamide (AC), followed by paclitaxel (T) compared with patients treated with anthracycline and cyclophosphamide (AC), followed by paclitaxel and trastuzumab (TH) treatment. The Figure illustrates the dramatic decrease in the Hazard of Distant Recurrence in the group receiving TH treatment.

Figure 11:
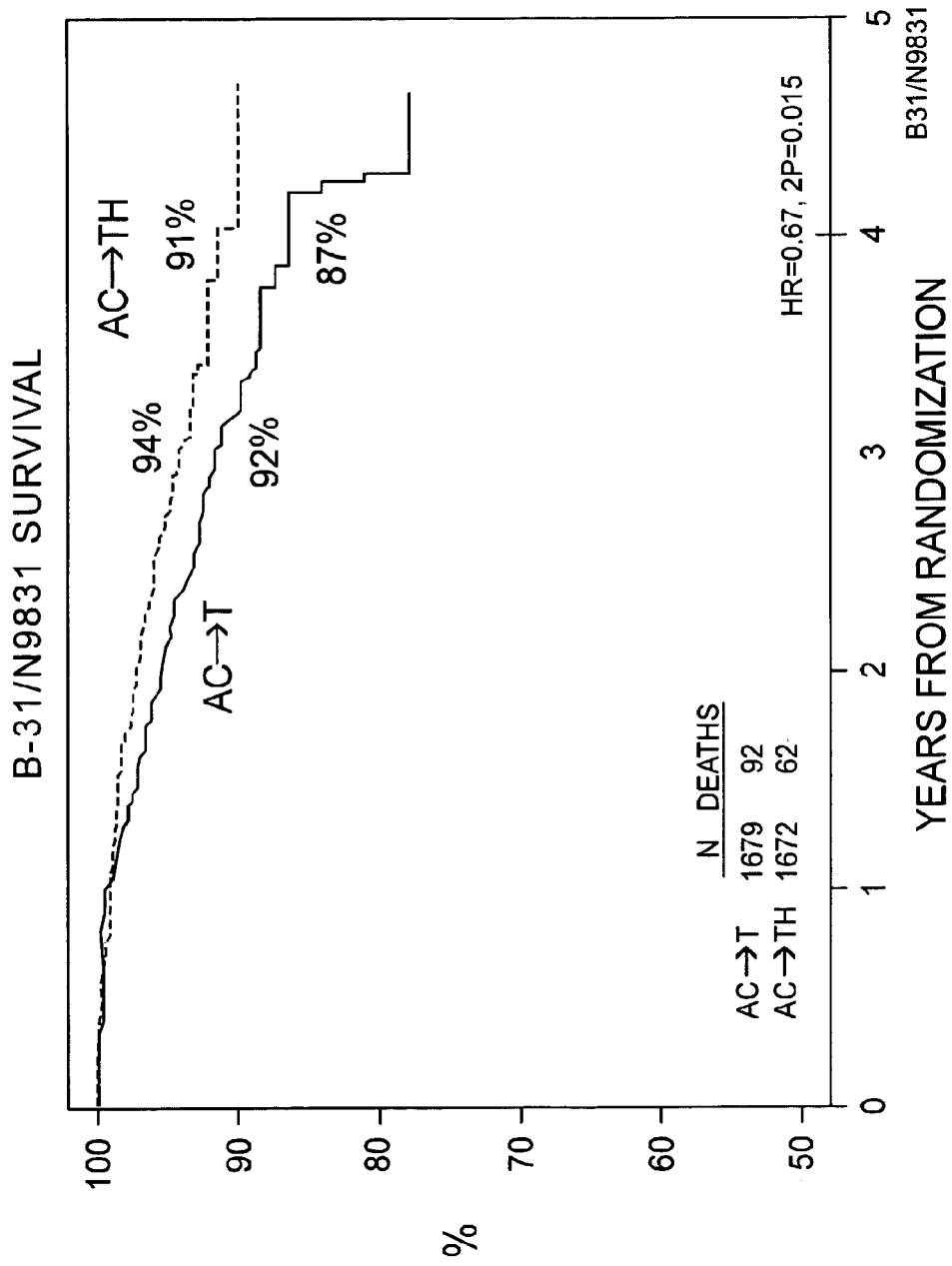
FIG. 11 shows survival data for the AC→T and AC→TH arms of the B31/N9831 studies.

Similarly, the survival data set forth in FIG. 11 show that the survival of patients in the TH-treated group significantly exceeded the survival of patients in the T-treated group. At 3 years from randomization, the AC+TH group was 94% vs. 92% of the AC+T group. The difference was even greater at 4 years: 91% in the AC+TH group vs. 87% in the AC+T group.

Efficacy endpoint analyses for the two studies are summarized in FIG. 12.

Figure 13:
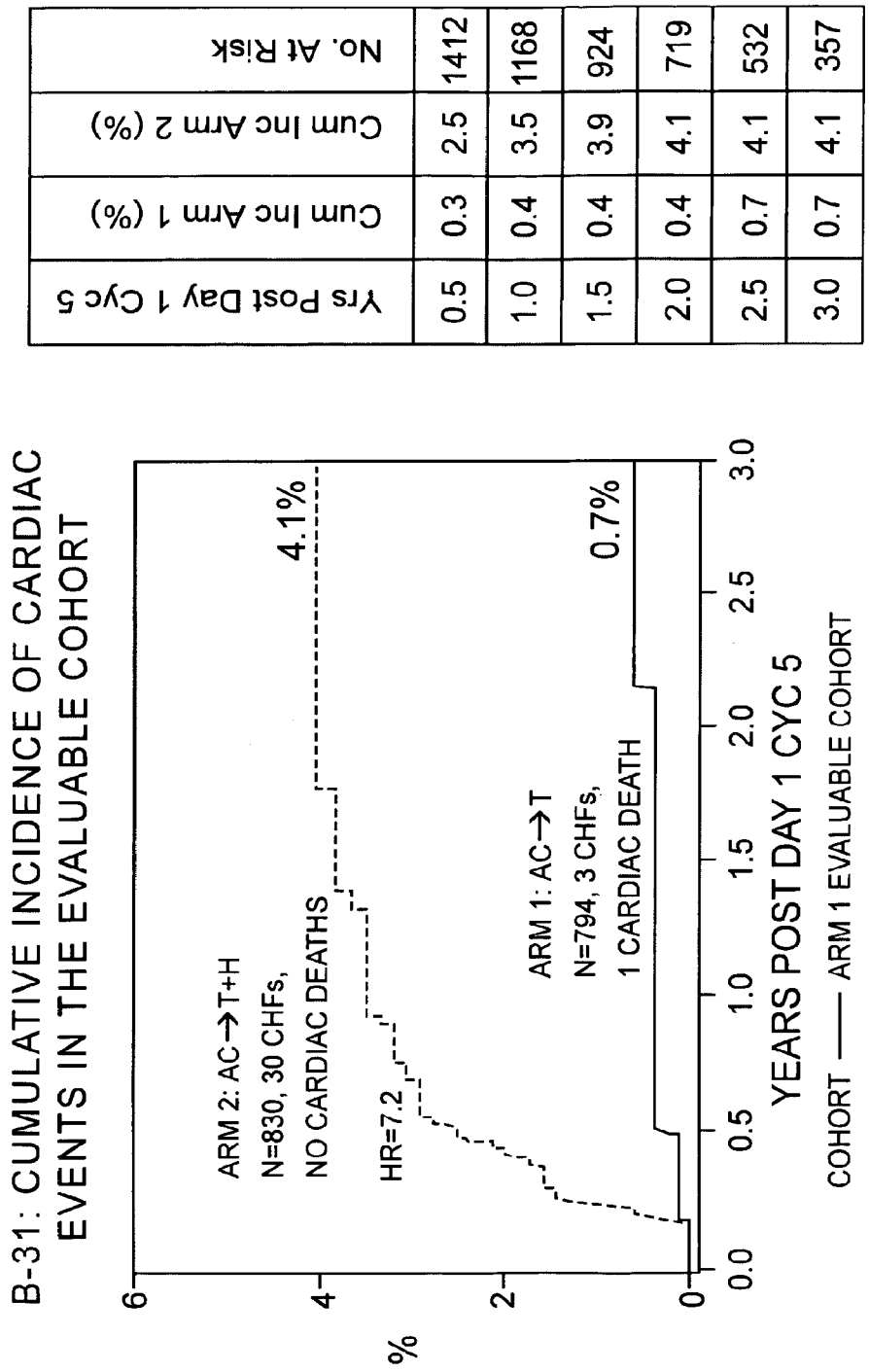
FIG. 13 presents the cumulative incidence of cardiac events in the evaluable cohort (for NSAPB B-31 study only).

The cumulative incidence of cardiac events in the evaluable cohort is depicted and summarized in FIG. 13.

Conclusions

For node positive HER2 positive breast cancer, trastuzumab given concurrently with paclitaxel following AC chemotherapy, reduced the risk of a first breast cancer event at 3 years by 52%.

The relative risk reduction benefit was present and of similar magnitude in all subsets of patients analyzed.

The addition of trastuzumab reduced the probability of distant recurrence by 53% at 3 years, and the hazard of developing distant metastases appeared to decrease over time.

Results at a median follow-up at 2 years show a statistically significant survival advantage with a relative risk reduction of 33%.

What is claimed is:

1. A method of adjuvant therapy comprising administering to a human subject having HER2 positive cancer, following definitive surgery, anthracycline cyclophosphamide (AC) based chemotherapy, followed by sequential administration of a taxoid and an effective amount of an immunoconjugate comprising an anti-ErbB2 antibody conjugated to a maytansinoid.

2. The method of claim 1, wherein the taxoid is paclitaxel or docetaxel.

3. The method of claim 1 wherein the anti-ErbB2 antibody specifically binds the extracellular domain of ErbB2.

4. The method of claim 3 wherein the anti-ErbB2 antibody specifically binds to the 4D5 epitope within the extracellular domain of ErbB2.

5. The method of claim 4 wherein the antibody is huMAb4D5-8.

6. The method of claim 5 wherein the maytansinoid is DM1 having the following structure and wherein the antibody is chemically linked to the maytansinoid via a disulfide or thioether group at "R" shown in the structure.

7. The method of claim 5, wherein the immunoconjugate comprises from 3 to 5 maytansinoid molecules per antibody molecule.

8. The method of claim 5, wherein the antibody and the maytansinoid are conjugated by a chemical linker selected from N-succinimidyl-3-(2-pyridyldithio)propionate, N-succinimidyl-4-(2-pyridylthio)pentanoate (SPP) and succinimidyl-4-(N-maleimidomethyl)cyclohexane-1-carboxylate (SMCC).

9. The method of claim 6 or 8, wherein the antibody and the maytansinoid are conjugated by succinimidyl-4-(N-maleimidomethyl)cyclohexane-1-carboxylate.

10. The method of claim 5, wherein the HER2 positive cancer is HER2 positive breast cancer.

11. The method of claim 1, claim 5, or claim 10, wherein said administration extends disease free survival (DFS) or overall survival (OS) in the subject.

12. The method of claim 10, wherein the HER2 positive cancer is nonmetastatic HER2 positive breast cancer.

13. The method of claim 10, wherein the immunoconjugate is administered in combination with an anti-ErbB2 antibody.

14. The method of claim 13, wherein the anti-ErbB2 antibody is a HER2 dimerization inhibitor.

15. The method of claim 14, wherein the HER2 dimerization inhibitor is pertuzumab.

* * * * *

SEQUENCE LISTING

<160> NUMBER OF SEQ ID NOS: 8

<210> SEQ ID NO 1
<211> LENGTH: 195
<212> TYPE: PRT
<213> ORGANISM: Homo sapiens

<400> SEQUENCE: 1

```
Thr Gln Val Cys Thr Gly Thr Asp Met Lys Leu Arg Leu Pro Ala
 1               5                  10                  15

Ser Pro Glu Thr His Leu Asp Met Leu Arg His Leu Tyr Gln Gly
                20                  25                  30

Cys Gln Val Val Gln Gly Asn Leu Glu Leu Thr Tyr Leu Pro Thr
                35                  40                  45

Asn Ala Ser Leu Ser Phe Leu Gln Asp Ile Gln Glu Val Gln Gly
                50                  55                  60

Tyr Val Leu Ile Ala His Asn Gln Val Arg Gln Val Pro Leu Gln
                65                  70                  75

Arg Leu Arg Ile Val Arg Gly Thr Gln Leu Phe Glu Asp Asn Tyr
                80                  85                  90

Ala Leu Ala Val Leu Asp Asn Gly Asp Pro Leu Asn Asn Thr Thr
                95                 100                 105

Pro Val Thr Gly Ala Ser Pro Gly Gly Leu Arg Glu Leu Gln Leu
               110                 115                 120

Arg Ser Leu Thr Glu Ile Leu Lys Gly Gly Val Leu Ile Gln Arg
               125                 130                 135

Asn Pro Gln Leu Cys Tyr Gln Asp Thr Ile Leu Trp Lys Asp Ile
               140                 145                 150

Phe His Lys Asn Asn Gln Leu Ala Leu Thr Leu Ile Asp Thr Asn
               155                 160                 165

Arg Ser Arg Ala Cys His Pro Cys Ser Pro Met Cys Lys Gly Ser
               170                 175                 180

Arg Cys Trp Gly Glu Ser Ser Glu Asp Cys Gln Ser Leu Thr Arg
```

-continued

```
              185                 190                 195
```

<210> SEQ ID NO 2
<211> LENGTH: 124
<212> TYPE: PRT
<213> ORGANISM: Homo sapiens

<400> SEQUENCE: 2

```
Thr Val Cys Ala Gly Gly Cys Ala Arg Cys Lys Gly Pro Leu Pro
 1               5                  10                  15

Thr Asp Cys Cys His Glu Gln Cys Ala Ala Gly Cys Thr Gly Pro
                20                  25                  30

Lys His Ser Asp Cys Leu Ala Cys Leu His Phe Asn His Ser Gly
                35                  40                  45

Ile Cys Glu Leu His Cys Pro Ala Leu Val Thr Tyr Asn Thr Asp
                50                  55                  60

Thr Phe Glu Ser Met Pro Asn Pro Glu Gly Arg Tyr Thr Phe Gly
                65                  70                  75

Ala Ser Cys Val Thr Ala Cys Pro Tyr Asn Tyr Leu Ser Thr Asp
                80                  85                  90

Val Gly Ser Cys Thr Leu Val Cys Pro Leu His Asn Gln Glu Val
                95                 100                 105

Thr Ala Glu Asp Gly Thr Gln Arg Cys Glu Lys Cys Ser Lys Pro
               110                 115                 120

Cys Ala Arg Val
```

<210> SEQ ID NO 3
<211> LENGTH: 169
<212> TYPE: PRT
<213> ORGANISM: Homo sapiens

<400> SEQUENCE: 3

```
Cys Tyr Gly Leu Gly Met Glu His Leu Arg Glu Val Arg Ala Val
 1               5                  10                  15

Thr Ser Ala Asn Ile Gln Glu Phe Ala Gly Cys Lys Lys Ile Phe
                20                  25                  30

Gly Ser Leu Ala Phe Leu Pro Glu Ser Phe Asp Gly Asp Pro Ala
                35                  40                  45

Ser Asn Thr Ala Pro Leu Gln Pro Glu Gln Leu Gln Val Phe Glu
                50                  55                  60

Thr Leu Glu Glu Ile Thr Gly Tyr Leu Tyr Ile Ser Ala Trp Pro
                65                  70                  75

Asp Ser Leu Pro Asp Leu Ser Val Phe Gln Asn Leu Gln Val Ile
                80                  85                  90

Arg Gly Arg Ile Leu His Asn Gly Ala Tyr Ser Leu Thr Leu Gln
                95                 100                 105

Gly Leu Gly Ile Ser Trp Leu Gly Leu Arg Ser Leu Arg Glu Leu
               110                 115                 120

Gly Ser Gly Leu Ala Leu Ile His His Asn Thr His Leu Cys Phe
               125                 130                 135

Val His Thr Val Pro Trp Asp Gln Leu Phe Arg Asn Pro His Gln
               140                 145                 150

Ala Leu Leu His Thr Ala Asn Arg Pro Glu Asp Glu Cys Val Gly
               155                 160                 165

Glu Gly Leu Ala
```

```
<210> SEQ ID NO 4
<211> LENGTH: 142
<212> TYPE: PRT
<213> ORGANISM: Homo sapiens

<400> SEQUENCE: 4

Cys His Gln Leu Cys Ala Arg Gly His Cys Trp Gly Pro Gly Pro
 1               5                  10                  15

Thr Gln Cys Val Asn Cys Ser Gln Phe Leu Arg Gly Gln Glu Cys
            20                  25                  30

Val Glu Glu Cys Arg Val Leu Gln Gly Leu Pro Arg Glu Tyr Val
        35                  40                  45

Asn Ala Arg His Cys Leu Pro Cys His Pro Glu Cys Gln Pro Gln
    50                  55                  60

Asn Gly Ser Val Thr Cys Phe Gly Pro Glu Ala Asp Gln Cys Val
65                  70                  75

Ala Cys Ala His Tyr Lys Asp Pro Pro Phe Cys Val Ala Arg Cys
            80                  85                  90

Pro Ser Gly Val Lys Pro Asp Leu Ser Tyr Met Pro Ile Trp Lys
        95                  100                 105

Phe Pro Asp Glu Glu Gly Ala Cys Gln Pro Cys Pro Ile Asn Cys
    110                 115                 120

Thr His Ser Cys Val Asp Leu Asp Asp Lys Gly Cys Pro Ala Glu
125                 130                 135

Gln Arg Ala Ser Pro Leu Thr
            140

<210> SEQ ID NO 5
<211> LENGTH: 214
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Arg Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

His Tyr Thr Thr Pro Pro Thr Phe Gly Gln Gly Thr Lys Val Glu
        95                  100                 105

Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu
125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
        155                 160                 165
```

```
Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 6
<211> LENGTH: 449
<212> TYPE: PRT
<213> ORGANISM: Artificial sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ser Arg Trp Gly Gly Asp Gly Phe Tyr
                 95                 100                 105

Ala Met Asp Tyr Trp Gly Gln Gly Thr Leu Val Thr Val Ser Ser
                110                 115                 120

Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
                155                 160                 165

Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300
```

```
Ser Thr Tyr Arg Val Val Ser Val Leu Thr Val Leu His Gln Asp
            305                 310                 315

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly
            440                 445

<210> SEQ ID NO 7
<211> LENGTH: 214
<212> TYPE: PRT
<213> ORGANISM: Artificial sequence
<220> FEATURE:
<223> OTHER INFORMATION: sequence is synthesized

<400> SEQUENCE: 7

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195
```

-continued

Val Thr His Gln Gly Leu Ser Ser Pro Val Thr Lys Ser Phe Asn
                200                 205                 210

Arg Gly Glu Cys

<210> SEQ ID NO 8
<211> LENGTH: 448
<212> TYPE: PRT
<213> ORGANISM: Artificial sequence
<220> FEATURE:
<223> OTHER INFORMATION: sequence is synthesized

<400> SEQUENCE: 8

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
                 20                  25                  30

Asp Tyr Thr Met Asp Trp Val Arg Gln Ala Pro Gly Lys Gly Leu
                 35                  40                  45

Glu Trp Val Ala Asp Val Asn Pro Asn Ser Gly Gly Ser Ile Tyr
                 50                  55                  60

Asn Gln Arg Phe Lys Gly Arg Phe Thr Leu Ser Val Asp Arg Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asn Leu Gly Pro Ser Phe Tyr
                 95                 100                 105

Phe Asp Tyr Trp Gly Gln Gly Thr Leu Val Thr Val Ser Ser Ala
                110                 115                 120

Ser Thr Lys Gly Pro Ser Val Phe Pro Leu Ala Pro Ser Ser Lys
                125                 130                 135

Ser Thr Ser Gly Gly Thr Ala Ala Leu Gly Cys Leu Val Lys Asp
                140                 145                 150

Tyr Phe Pro Glu Pro Val Thr Val Ser Trp Asn Ser Gly Ala Leu
                155                 160                 165

Thr Ser Gly Val His Thr Phe Pro Ala Val Leu Gln Ser Ser Gly
                170                 175                 180

Leu Tyr Ser Leu Ser Ser Val Val Thr Val Pro Ser Ser Ser Leu
                185                 190                 195

Gly Thr Gln Thr Tyr Ile Cys Asn Val Asn His Lys Pro Ser Asn
                200                 205                 210

Thr Lys Val Asp Lys Lys Val Glu Pro Lys Ser Cys Asp Lys Thr
                215                 220                 225

His Thr Cys Pro Pro Cys Pro Ala Pro Glu Leu Leu Gly Gly Pro
                230                 235                 240

Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp
                305                 310                 315

Leu Asn Gly Lys Glu Tyr Lys Cys Lys Val Ser Asn Lys Ala Leu
                320                 325                 330

```
Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445
```